US012723069B2

(12) United States Patent
Emrich et al.

(10) Patent No.: US 12,723,069 B2
(45) Date of Patent: Sep. 1, 2026

(54) MODIFICATION OF ANTIBODY FcRn BINDING

(71) Applicant: Hoffmann-La Roche Inc., Little Falls, NJ (US)

(72) Inventors: Thomas Emrich, Iffeldorf (DE); Hubert Kettenberger, Munich (DE); Thomas Kraft, Munich (DE); Wolfgang Richter, Lorrach (DE); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1306 days.

(21) Appl. No.: 17/237,426

(22) Filed: Apr. 22, 2021

(65) Prior Publication Data

US 2022/0073593 A1 Mar. 10, 2022

Related U.S. Application Data

(63) Continuation of application No. PCT/EP2019/078970, filed on Oct. 24, 2019.

(30) Foreign Application Priority Data

Oct. 25, 2018 (EP) .................................... 18202631

(51) Int. Cl.
*C07K 16/00* (2006.01)
*A61K 39/00* (2006.01)
*B01D 15/38* (2006.01)

(52) U.S. Cl.
CPC .......... *C07K 16/00* (2013.01); *B01D 15/3809* (2013.01); *A61K 2039/505* (2013.01); *C07K 2317/55* (2013.01); *C07K 2317/56* (2013.01); *C07K 2317/72* (2013.01); *C07K 2317/94* (2013.01)

(58) Field of Classification Search
CPC ...... C07K 2317/94; C07K 1/22; C07K 16/00; C07K 2317/55; C07K 2317/56; C07K 2317/72; C07K 2317/567; B01D 15/3809; A61K 2039/505
See application file for complete search history.

(56) References Cited

U.S. PATENT DOCUMENTS

| | | | | |
|---|---|---|---|---|
| 9,975,953 | B2 | 5/2018 | Micklem et al. | |
| 11,668,722 | B2 * | 6/2023 | Kettenberger | C07K 16/18 436/501 |
| 2005/0032114 | A1 | 2/2005 | Hinton et al. | |
| 2007/0148164 | A1 | 6/2007 | Farrington et al. | |
| 2009/0148437 | A1 | 6/2009 | Cook et al. | |
| 2010/0162418 | A1 | 6/2010 | Kanda et al. | |
| 2014/0112914 | A1 | 4/2014 | Nezu et al. | |
| 2014/0348839 | A1 | 11/2014 | Chowdhury et al. | |
| 2016/0031985 | A1 | 2/2016 | Bowdish et al. | |
| 2016/0194389 | A1 | 7/2016 | Regula et al. | |
| 2016/0229908 | A1 | 8/2016 | Igawa et al. | |
| 2017/0037121 | A1 | 2/2017 | Schlothauer et al. | |
| 2017/0204157 | A1 | 7/2017 | Wang et al. | |
| 2017/0227547 | A1 | 8/2017 | Emrich et al. | |
| 2017/0342167 | A1 | 11/2017 | Moessner et al. | |

FOREIGN PATENT DOCUMENTS

| | | | | |
|---|---|---|---|---|
| CN | 1942481 A | 4/2007 | | |
| CN | 103429737 A | 12/2013 | | |
| CN | 105143262 A | 9/2015 | | |
| CN | 105164157 A | 12/2015 | | |
| CN | 106103478 A | 9/2016 | | |
| CN | 106459191 A | 2/2017 | | |
| KR | 10-2014-0127251 | 11/2014 | | |
| RU | 2010130851 A1 | 2/2012 | | |
| WO | 2005/100395 A2 | 10/2005 | | |
| WO | 2009/086320 A1 | 9/2009 | | |
| WO | 2013/120929 A1 | 8/2013 | | |
| WO | 2014/177459 A2 | 6/2014 | | |
| WO | 2014/177460 A1 | 6/2014 | | |
| WO | 2015/140126 A1 | 9/2015 | | |
| WO | 2015/189249 A1 | 12/2015 | | |
| WO | WO-2017186928 A1 * | 11/2017 | ......... | C07K 16/1282 |
| WO | 2018/184966 A1 | 10/2018 | | |

OTHER PUBLICATIONS

Goulet et al (Toward a Combinatorial Approach for the Prediction of IgG Half-Life and Clearance. Drug Metab Dispos. Dec. 2018;46(12):1900-1907. doi: 10.1124/dmd.118.081893. Epub Sep. 19, 2018) (Year: 2018).*

Stapleton et al (Nature Communications, DOI: 10.1038/ncomms1608, published Dec. 20, 2011) (Year: 2011).*

Cymer et al (Evaluation of an FcRn Affinity Chromatographic Method for Igg1-Type Antibodies and Evaluation of Igg Variants. Bioanalysis, 9(17), 1305-1317) (Year: 2017).*

Reverso (Producing; obtained from: https://dictionary.reverso.net/english-definition/producing (accessed Apr. 17, 2026; see screen capture for proof of availability as of Apr. 18, 2018) (Year: 2018).*

Reverso screen capture for proof of date of availability (Year: 2018).*

Burvenich et al (Biochem J Jul. 16, 2018; 475 (13): 2179-2190. doi: https://doi.org/10.1042/BCJ20180139 (Year: 2018).*

(Continued)

*Primary Examiner* — Gregory S Emch
*Assistant Examiner* — Ashley H. Gao
(74) *Attorney, Agent, or Firm* — Kathleen Robinson

(57) ABSTRACT

Herein is reported a method for providing a modified antibody with improved in vivo half-live, comprising the modification of the Fc-region of the antibody by introducing one or more mutations that change the binding of the Fc-region to human FcRn until the (relative) retention time of the modified antibody in an FcRn affinity chromatography is increased for more than 1 minute but not more than 5 minutes compared to the parent antibody.

7 Claims, 13 Drawing Sheets

Specification includes a Sequence Listing.

(56) References Cited

OTHER PUBLICATIONS

Akilesh et al., "Neonatal FcR Expression in Bone Marrow-Derived Cells Functions to Protect Serum IgG from Catabolism1" J Immunol 179:4580-4588 ( 2007).
Brambell et al. et al., "A Theoretical Model of γ-Globulin Catabolism" Nature 203:1352-1354 ( 1964).
Chaudhury et al., "The Major Histocompatibility Complex-related Fc Receptor for IgG (FcRn) Binds Albumin and Prolongs Its Lifespan" J. Exp. Med. 197:315-322 ( 2003).
Datta-Mannan et al., "The interplay of non-specific binding, target-mediated clearance and FcRn interactions on the pharmacokinetics of humanized antibodies" MABS 7(6):1084-1093 (2015).
Edelman et al., "Antibody structure and molecular immunology" J Immunol 34:1-22 ( 1991).
Ghetie and Ward, "Multiple Roles for the Major Histocompatibility Complex Class I-Related Receptor FcRn" Ann Rev Immunol 18:739-766 ( 2000).
Goebl et al., "Neonatal Fc Receptor Mediates Internalization of Fc in Transfected Human Endothelial Cells" Mol. Biol. Cell 19:5490-5505 ( 2008).
Hotzel et al., "A strategy for risk mitigation of antibodies with fast clearance" mAbs 4(6):753-760 ( 2012).
Huber et al., "Crystallization and stoichiometry of binding of a complex between a rat intestinal Fc receptor and Fc" J Mol Biol 230:1077-1083 ( 1993).
International Preliminary Report on Patentability for PCT/EP2019/078970 issued Apr. 27, 2021.
International Search Report for PCT/EP2019/078970 mailed on Jan. 30, 2020.
Kim et al., "Identifying amino acid residues that influence plasma clearance of murine IgG1 fragments by site-directed mutagenesis," Eur. J. Immunol. 24 (1994) 542-548.
Kuo et al., "Neonatal Fc Receptor: From Immunity to Therapeutics" J. Clin. Immunol. 30:777-789 ( 2010).
Martin et al., "Crystal structure at 2.8 A of an FcRn/heterodimeric Fc complex: mechanism of pH-dependent binding" Mol Cell 7(4):867-877 (Apr. 2001).
Montoyo et al., "Conditional deletion of the MHC class I-related receptor FcRn reveals the sites of IgG homeostasis in mice" PNAS 106:2788-2793 ( 2009).
Neuber et al., "Characterization and screening of IgG binding to the neonatal Fc receptor" mAbs 6(4):928-942 ( 2014).
Ober et al., "Exocytosis of IgG as mediated by the receptor, FcRn: an Analysis at the Single-Molecule Level" Proc Natl Acad Sci U.S.A. 101(30):11076-11081. (Jul. 2004).
Ober et al., "Visualizing the Site and Dynamics of IgG Salvage by the MHC Class I-Related Receptor, FcRn1" J Immunol 172:2021-2029 ( 2004).
Putnam et al., "Pharmacokinetic, pharmacodynamic and immunogenicity comparability assessment strategies for monoclonal antibodies" Trends Biotechnol 28:509-516 (2010).
Reff et al., "A review of modifications to recombinant antibodies: attempt to increase efficacy in oncology applications" Crit. Rev. Oncol. Hematol 40:25-35 ( 2001).
Rodewald et al., "ph-dependent binding of immunoglobulins to intestinal cells of the neonatal rat" J Cell Biol 71:666-669 (Nov. 1976).
Roopenian and Akilesh, "FcRn: the neonatal Fc receptor comes of age" Nat Rev Immunol 7:715-725 ( 2007).
Roopenian et al., "The MHC Class I-like IgG receptor controls perinatal IgG transport, IgG homestasis, and fate of IgG fc-copled drugs" J Immuno. 170(7):3528-3533 (Apr. 2003).
Sampei et al., "Identification and multidimensional optimization of an asymmetric bispecific IgG antibody mimicking the function of factor VIII cofactor activity" PLOS One 8(2):e57479 (2013).
Sanchez et al., "Stoichiometry of the Interaction between the Major Histocompatibility Complex-Related Fc Receptor and Its Fc Ligand" Biochemistry 38:9471-9476 ( 1999).
Schoch et al., "Charge-mediated influence of the antibody variable domain on FcRn-dependent pharmacokinetics" PNAS 112(19):5997-6002 ( 2015).
Vaccaro et al., "Engineering the Fc region of immunoglobulin G to modulate in vivo antibody levels" Nature Biotechnology 23:1283-1288 ( 2005).
Waldmann and Strober, "Metabolism of Immunoglobulins" Prog. Allergy 13:1-110 ( 1969).
Datta-Mannan, A., et al., "Balancing charge in the complementarity-determining regions of humanized mAbs without affecting pI reduces non-specific binding and improves the pharmacokinetics" MABS 7(3):483-493 ( 2015).
Shi, Y., et al., "Study on Pharmacokinetics of Eprinomectin in Sheep Following Intravenous and Subcutaneous Administration" Acta Veterinaria Et Zootechnica Sinica (Chinese w/Eng. Abstract), 36(3):292-295 (Mar. 25, 2005).
Tan, H., et al., "Strategies to Prolong the Half-Life of Therapeutic Peptides and Proteins" Chinese Pharm Bull (Chinese w/Eng. Abstract), 29(12): 1634-1639 (Dec. 2, 2013).
Syed, S., et al., "Potent Antithrombin Activity and Delayed Clearance from the Circulation Characterize Recombinant Hirudin Genetically Fused to Albumin" BLOOD 89(9):3243-3252 (May 1, 1997).

* cited by examiner

MODIFICATION OF ANTIBODY FcRn BINDING

CROSS REFERENCE TO RELATED APPLICATIONS

This application is a continuation of International Application No. PCT/EP2019/078970, filed Oct. 24, 2019, which is claims priority to European Patent Application No. 18202631.0, filed Oct. 25, 2018, which are incorporated herein by reference in its entirety.

SEQUENCE LISTING

This application contains a Sequence Listing which has been submitted electronically in ASCII format and is hereby incorporated by reference in its entirety. Said ASCII copy, created on Apr. 1, 2021, is named P35112-US-Sequence-Listing.txt and is 73,030 bytes bytes in size.

The current invention is in the field of recombinant antibody technology. Herein is reported a method for the modification of the pharmacokinetic properties of an antibody based Fv and Fc-region engineering.

BACKGROUND OF THE INVENTION

Human immunoglobulins of the class G (IgGs) contain two antigen binding (Fab) regions that convey specificity for the target antigen and a constant region (Fc-region) that is responsible for interactions with Fc receptors (see e.g. Edelman, G. M., Scand. J. Immunol. 34 (1991) 1-22; Reff, M. E. and Heard, C., Crit. Rev. Oncol. Hematol. 40 (2001) 25-35). Human IgGs of subclasses IgG1, IgG2 and IgG4 have an average serum half-life of 21 days, which is longer than that of any other known serum protein (see, e.g., Waldmann, T. A. and Strober, W., Prog. Allergy 13 (1969) 1-110). This long half-life is predominantly mediated by the interaction between the Fc-region and the neonatal Fc receptor (FcRn) (see, e.g. Ghetie, V. and Ward, E. S., Annu. Rev. Immunol. 18 (2000) 739-766; Chaudhury, C., et al., J. Exp. Med. 197 (2003) 315-322). This is one of the reasons, why IgGs or Fc-containing fusion proteins are used as a widespread class of therapeutics.

The neonatal Fc receptor FcRn is a membrane-associated receptor involved in both IgG and albumin homeostasis, in maternal IgG transport across the placenta and in antigen-IgG immune complex phagocytosis (see, e.g., Brambell, F. W., et al., Nature 203 (1964) 1352-1354; Ropeenian, D. C., et al., J. Immunol. 170 (2003) 3528-3533). Human FcRn is a heterodimer consisting of the glycosylated class I major histocompatibility complex-like protein (α-FcRn) and a $\beta_2$ microglobulin ($\beta_2$m) subunit (see, e.g., Kuo, T. T., et al., J. Clin. Immunol. 30 (2010) 777-789). FcRn binds to a site in the $C_H2$-$C_H3$ region of the Fc-region (see, e.g., Ropeenian, D. C. and Akilesh, S., Nat. Rev. Immunol. 7 (2007) 715-725; Martin, W. L., et al., Mol. Cell 7 (2001) 867-877; Goebl, N. A., et al., Mol. Biol. Cell 19 (2008) 5490-5505; Kim, J. K., et al., Eur. J. Immunol. 24 (1994) 542-548) and two FcRn molecules can bind to the Fc-region simultaneously (see, e.g., Sanchez, L. M., et al., Biochemistry 38 (1999) 9471-9476; Huber, A. H., et al., J. Mol. Biol. 230 (1993) 1077-1083). The affinity between the FcRn and the Fc-region is pH dependent, showing nanomolar affinity at endosomal pH of 5-6 and rather weak binding at a physiological pH of 7.4 (see, e.g., Goebl, N. A., et al., Mol. Biol. Cell 19 (2008) 5490-5505; Ober, R. J., et al., Proc. Natl. Acad. Sci. USA 101 (2004) 11076-11081; Ober, R. J., et al., J. Immunol. 172 (2004) 2021-2029). The underlying mechanism conveying long half-life to IgGs can be explained by three fundamental steps. First, IgGs are subject to unspecific pinocytosis by various cell types (see, e.g., Akilesh, S., et al., J. Immunol. 179 (2007) 4580-4588; Montoyo, H. P., et al., Proc. Natl. Acad. Sci. USA 106 (2009) 2788-2793). Second, IgGs encounter and bind FcRn in the acidic endosome at a pH of 5-6, thereby protecting IgGs from lysosomal degradation (see, e.g., Ropeenian, D. C. and Akilesh, S., Nat. Rev. Immunol. 7 (2007) 715-725; Rodewald, R., J. Cell Biol. 71 (1976) 666-669). Finally, IgGs are released in the extracellular space at physiological pH of 7.4 (see, e.g., Ghetie, V. and Ward, E. S., Annu. Rev. Immunol. 18 (2000) 739-766). This strict pH-dependent bind-and-release mechanism is critical for IgG recycling and any deviation of the binding characteristics at different pH values may strongly influence circulation half-life of IgGs (see, e.g., Vaccaro, C., et al., Nat. Biotechnol. 23 (2005) 1283-1288).

Hoetzel, I., et al. (mAbs 4 (2012) 753-760) disclosed a strategy for risk mitigation of antibodies with fast clearance as a majority of human therapeutic antibody candidates show pharmacokinetic properties suitable for clinical use, but an unexpectedly fast antibody clearance is sometimes observed that may limit the clinical utility. It is described an assay based on ELISA detection of binding to baculovirus (BV) particles to evaluate the non-specific binding of therapeutic proteins.

Analytical FcRn affinity chromatography for functional characterization of monoclonal antibodies is disclosed in WO 2013/120929. Pharmacokinetic, pharmacodynamic and immunogenicity comparability assessment strategies for monoclonal antibodies are disclosed by Putnam, W. S., et al. (Trends Biotechnol. 28 (2010) 509-516).

Sampei, Z., et al. (PLOS One 8 (2013) e57479) disclose the identification and multidimensional optimization of an asymmetric bispecific IgG antibody mimicking the function of factor VIII cofactor activity.

WO 2015/140126 discloses a method for the prediction of the in vivo half-life of an antibody based on the retention time determined on an FcRn affinity chromatography column.

Current literature discloses the use of FcRn chromatography (see, e.g., Schoch, A., et al., Proc. Natl. Acad. Sci. USA 112 (2015) 5997-6002) or FcRn affinity (see, e.g., Neuber, T., et al., MAbs 6 (2014) 928-942) as predictive for pharmacokinetics. Alternatively, heparin binding, e.g. in ELISA format (see, e.g., Datta-Mannan, A., et al., MAbs 7 (2015) 1084-1093) is disclosed as a surrogate parameter to quantify non-specific interactions with cell surface structures.

WO 2015/189249 discloses a method for selecting antibodies with modified FcRn interaction. Fc-receptor binding modified asymmetric antibodies and methods of use are disclosed in US 2016/019489. In US 2017/227547 the in vitro prediction of in vivo half-life is disclosed. Antibodies binding to STEAP-1 are disclosed in WO 2018/184966.

SUMMARY OF THE INVENTION

With the method according to the current invention it is possible to modify the pharmacokinetic properties of an antibody by Fv and/or Fc-region engineering. Thus, it is possible with the method according to the invention to adjust the pharmacokinetic properties for a given antibody to the respective therapeutic application. Especially it is possible to reduce clearance and thereby increase the in vivo half-live of an antibody, i.e. to improve its pharmacokinetic properties, to make it more suitable for a therapeutic application. This is done by modifying the charge distribution in the Fv and the FcRn-binding in the Fc-region based on the disclosure provided herein.

The method according to the invention is based on the combination of two different chromatographic methods, i.e. the combination of FcRn affinity chromatography and heparin affinity chromatography. The combination of FcRn affinity chromatography and heparin affinity chromatography allows defining FcRn and heparin affinity chromatography column retention time thresholds and thereby a two-dimensional retention time region, wherein antibodies with slow clearance, i.e. long systemic circulation half-live, can be found.

It has been found that for improving the pharmacokinetic properties of an antibody by introducing modifications in the Fc-region an increase of the retention time in an FcRn affinity chromatography by 1 minute or more but less than about 5 minutes provides for the most efficient modification with respect to improving the in vivo half-live. In one preferred embodiment the increase is more than 3 minutes but less than 4 minutes.

Thus, herein is reported a method for providing a modified antibody with improved in vivo half-live, comprising the modification of the Fc-region of the antibody by introducing one or more mutations that change the binding of the Fc-region to human FcRn until the (relative) retention time of the modified antibody in an FcRn affinity chromatography is increased for more than 1 minute but not more than 5 minutes compared to the parent antibody.

Thus, one aspect of the current invention is a method for providing an antibody with improved in vivo half-live, comprising the following steps:

a) determining the (relative) retention time of a (parent) antibody in an FcRn affinity chromatography,
b) modifying the Fc-region of the antibody by introducing mutations that increase the binding of the Fc-region to human FcRn to obtain a modified antibody,
c) determining the (relative) retention time of the modified antibody in an FcRn affinity chromatography,
d) repeating step b) if the change of the relative retention time between the (parent) antibody and the modified antibody is less than about 1 minute and more than about 5 minutes, whereby in case the change of the relative retention time is less than 1 minute mutations are chosen that result in a further increased binding of the Fc-region to human FcRn or in case the change of the relative retention time is more than 5 minutes mutations are chosen that result in a less increased binding of the Fc-region to human FcRn compared to the parent antibody,
e) providing an antibody with improved in vivo half-live if the change of the relative retention time between the (parent) antibody and the modified antibody is more than about 1 minute and less than about 5 minutes.

This aspect may be alternatively worded: one aspect of the current invention is a method for providing an antibody with improved in vivo half-live, comprising the following steps:

a) determining the (relative) retention time of a (parent) antibody in an FcRn affinity chromatography,
b) modifying the Fc-region of the antibody by introducing mutations that increase the binding of the Fc-region to human FcRn to obtain a modified antibody,
c) determining the (relative) retention time of the modified antibody in an FcRn affinity chromatography, wherein/characterized in that step b) is repeated if the change of the relative retention time between the (parent) antibody and the modified antibody is less than about 1 minute and more than about 5 minutes, whereby in case the change of the relative retention time is less than 1 minute mutations are chosen that result in a further increased binding of the Fc-region to human FcRn or in case the change of the relative retention time is more than 5 minutes mutations are chosen that result in a less increased binding of the Fc-region to human FcRn compared to the parent antibody, whereby/characterized in that an antibody with improved in vivo half-live is provided if the change of the relative retention time between the (parent) antibody and the modified antibody is more than about 1 minute and less than about 5 minutes.

In one embodiment the change of the relative retention time between the (parent) antibody and the modified antibody is more than about 2 minute and less than about 4.5 minutes.

In one embodiment the change of the relative retention time between the (parent) antibody and the modified antibody is more than about 3 minute and less than about 4 minutes.

In one embodiment the change of the relative retention time between the (parent) antibody and the modified antibody is more than about 3.3 minute and less than about 3.9 minutes.

In one embodiment the FcRn affinity chromatography is performed as follows:

an FcRn affinity chromatography column comprising about 1 mL of a streptavidin agarose matrix with human FcRn conjugated thereto via biotin-streptavidin non-covalent interaction (in one preferred embodiment with 1 mg to 5 mg FcRn per g matrix, preferably 2.5 mg FcRn per g matrix) is equilibrated with 80 vol-% buffer A (20 mM MES sodium salt, 140 mM NaCl, pH 5.5) and 20 vol-% buffer B (20 mM Tris/HCl, 140 mM NaCl, pH 8.8) at a flow rate of 0.5 mL/min and a column temperature of 25° C.;

a total of 30 μg of the antibody is prepared in the same mixture of 80 vol-% buffer A and 20 vol-% buffer B and injected on the equilibrated column;

ten minutes post injection, a linear gradient from 20 vol-% to 100 vol-% buffer B over 70 minutes is started;

optionally 100 vol-% buffer B is held for 10 minutes before the column is re-equilibrated with 80 vol-% buffer A and 20 vol-% buffer B;

whereby detection is performed with a UV detector set at 280 nm;

whereby (in order to make results from different runs and different buffer and column lots comparable, and to compensate for slight retention time drifts, a standard sample is measured at the beginning and the end of each sequence and after every $10^{th}$ run) a relative retention time on the FcRn affinity chromatography column is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak2}$: retention time of peak 2 of a partially oxidized anti-Her3 antibody according to FIG. 1; $t_{peak3}$: retention time of peak 3 of the anti-Her3 antibody according to FIG. 1).

In one embodiment the relative retention time on the FcRn affinity chromatography column is calculated according to the following equation:

$$t_{rel,i} = \frac{t_i - t_{peak2}}{t_{peak3} - t_{peak2}}$$

with $t_{rel,i}$: relative retention time of peak i; $t_i$: retention time of peak i; $t_{peak2}$: retention time of the second peak of a partially oxidized anti-Her3 antibody; $t_{peak3}$: retention time of the third peak of a partially oxidized anti-Her3 antibody on an FcRn affinity chromatography column with a gradient as outlined before/above in this embodiment. In one embodiment the anti-Her3 antibody has a heavy chain of SEQ ID NO: 03 and a light chain of SEQ ID NO: 04.

In one embodiment the FcRn is a non-covalent complex with human beta-2-microglobulin (b2m).

In one embodiment the method comprises as step b) the following step:

- b) modifying the Fc-region of the antibody by introducing mutations that increase the binding of the Fc-region to human FcRn to obtain a modified antibody,
  and
  modifying the Fv of the antibody by
  - reducing the size of positively charged patches,
  - reducing the size of positively charged patches and increasing the size of negatively charged patches,
  - making the overall distribution of the charges more even/evenly distributing the overall charges in the Fv or Fab.

In one embodiment the charge distribution in the Fv fragment is changed by

- i) changing at least one (permanently) negatively charged or not charged amino acid residue to a (permanently) positively charged amino acid residue, or
- ii) changing at least one (permanently) positively charged or not charged amino acid residue to a (permanently) negatively charged amino acid residue, or
- iii) changing at least one (permanently) charged amino acid residue to an amino acid residue with the opposite charge, or
- iv) changing at least one permanently charged amino acid residue to a pH-dependently charged amino acid residue, or
- v) a combination of i) to iv).

When the retention times on an FcRn affinity chromatography column and on a heparin affinity chromatography column are normalized based on the retention times of reference antibodies on the respective columns, a relative retention time region comprising predominantly antibodies with slow clearance is defined. This region is defined by a relative retention time on the FcRn affinity chromatography column of less than 1.78 (with an oxidized (H2O2-treated) anti-Her3 antibody preparation as reference antibody) and by a relative retention time on the heparin affinity chromatography column of less than 0.87 (with an anti-pTau antibody as reference antibody).

In one embodiment the method further comprises the following steps:

- e) performing an FcRn affinity chromatography with a positive linear pH gradient and a heparin affinity chromatography with a positive linear conductivity/salt gradient with the parent antibody and the modified antibody, and

- f) providing an antibody with improved in vivo half-live if the modified antibody has
  - i) a relative retention time on the FcRn affinity chromatography column that is less than the retention time of the parent antibody on the (same) FcRn affinity chromatography column (under the same elution conditions), or
  - ii) a relative retention time on the heparin affinity chromatography column that is less than the retention time of the parent antibody on the (same) heparin affinity chromatography column (under the same elution conditions), or
  - iii) both of i) and ii).

In one embodiment the method further comprises the following steps:

- e) performing an FcRn affinity chromatography with a positive linear pH gradient and a heparin affinity chromatography with a positive linear conductivity/salt gradient with the parent antibody and the modified antibody, and

- f) providing an antibody with improved in vivo half-live if the modified antibody has
  - i) a relative retention time on the FcRn affinity chromatography column that is more than the retention time of the parent antibody on the (same) FcRn affinity chromatography column (under the same elution conditions), or
  - ii) a relative retention time on the heparin affinity chromatography column that is more than the retention time of the parent antibody on the (same) heparin affinity chromatography column (under the same elution conditions), or
  - iii) both of i) and ii).

In one embodiment the method further comprises the following steps:

- e) performing an FcRn affinity chromatography with a positive linear pH gradient and a heparin affinity chromatography with a positive linear conductivity/salt gradient with the parent antibody and the modified antibody, and

- f) providing an antibody with improved in vivo half-live if the modified antibody has
  - i) a relative retention time on the FcRn affinity chromatography column that is less or more than the retention time of the parent antibody on the (same) FcRn affinity chromatography column (under the same elution conditions), or
  - ii) a relative retention time on the heparin affinity chromatography column that is less or more than the retention time of the parent antibody on the (same) heparin affinity chromatography column (under the same elution conditions), or
  - iii) both of i) and ii), wherein in i) the relative retention time is less and ii) it is more, or vice versa.

To determine charged patches on the (solvent exposed) surface of an antibody different methods and tools are known to a person skilled in the art. There are tools provided by different vendors or academic groups. For example, herein an in-silico calculation method based on the X-ray structure or a homology model, followed by pH-protonation of acidic and basic amino acid side-chains and calculation of the 3D charge distribution using the software CHARMM and Delphi as implemented in the software suite Discovery Studio (vendor: Dassault Systems) was used.

In one embodiment the modified antibody has at least one additional negatively charged patch on its (solvent-exposed) surface.

In one embodiment the modified antibody has the same (surface) net charge as the parent antibody.

In one embodiment a (permanently) negatively charged amino acid residue is selected from the group consisting of glutamate and aspartate.

In one embodiment a (permanently) positively charged amino acid residue is selected from the group consisting of arginine and lysine.

In one embodiment the pH-dependently charged amino acid residue is histidine.

In one embodiment a permanently charged amino acid residue has the same (net) charge in the pH range from pH 6 to pH 8.

In one embodiment a pH-dependently charged amino acid residue has a first (net) charge at pH 6 and an opposite second (net) charge at pH 8.

In one embodiment the standard sample is an oxidized antibody preparation comprising the reference antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono\text{-}oxidized\ peak}}{t_{reference\ antibody\ non\text{-}oxidized\ peak} - t_{reference\ antibody\ mono\text{-}oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04.

In one embodiment the first threshold value in step f) is 2. In one embodiment the first threshold value is 1.8. In one embodiment the first threshold value is 1.78. In one embodiment the second reference antibody in step f) is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment step f) is providing an antibody with improved in vivo half-live if the modified antibody has i) a relative retention time on the FcRn affinity chromatography column is less than 1.78 times the retention time difference between peaks 2 and 3 of a preparation of an oxidized anti-Her3 antibody of SEQ ID NO: 03 and 04, and ii) a relative retention time on the heparin affinity chromatography column is less than 0.87 times the retention time of an anti-pTau antibody of SEQ ID NO: 01 and 02.

In one embodiment of all methods the relative retention time on the FcRn affinity chromatography column is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak\ 2}$: retention time of peak 2 of the partially oxidized anti-Her3 antibody according to FIG. 1; $t_{peak\ 3}$: retention time of peak 3 of the anti-Her3 antibody according to FIG. 1).

In one embodiment of all methods the relative retention time on the heparin affinity chromatography column is calculated according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

In one embodiment in the FcRn affinity chromatography of step e) with a positive linear pH gradient is used an immobilized non-covalent complex of a neonatal Fc receptor (FcRn) and beta-2-microglobulin (b2m) as affinity chromatography ligand, wherein the non-covalent complex of a neonatal Fc receptor and beta-2-microglobulin is bound to a chromatography material and the non-covalent complex is conjugated to the solid phase via a specific binding pair, wherein the pH gradient is from a first pH value to a second pH value whereby the first pH value is from pH 3.5 to pH 6.4 and the second pH value is from pH 7.4 to pH 9.5, and wherein the non-covalent complex of a neonatal Fc receptor (FcRn) and beta-2-microglobulin (b2m) is mono-biotinylated and the solid phase is derivatized with streptavidin.

In one embodiment the pH gradient of step e) is from a first pH value to a second pH value whereby the first pH value is pH 5.5 and the second pH value is pH 8.8.

In one embodiment the beta-2-microglobulin is from the same species as the FcRn.

In one embodiment the FcRn is selected from human FcRn, cynomolgus FcRn, mouse FcRn, rat FcRn, sheep FcRn, dog FcRn, pig FcRn, minipig FcRn, and rabbit FcRn.

In one embodiment the beta-2-microglobulin is from the same species as the FcRn. In one embodiment the beta-2-microglobulin is from a different species as the FcRn.

In general, the soluble extracellular domain of FcRn (SEQ ID NO: 31 for human FcRn) with C-terminal His-Avi Tag (SEQ ID NO: 32) was co-expressed with β2-microglobulin (SEQ ID NO: 33 for human beta-2-microglobulin) in mammalian cells. The non-covalent FcRn-microglobulin complex was biotinylated and loaded onto streptavidin derivatized sepharose.

In one embodiment the reference antibody for the FcRn affinity chromatography is the anti-HER3 antibody with SEQ ID NO: 03 (heavy chain) and SEQ ID NO: 04 (light chain).

In one embodiment the reference antibody for the heparin affinity chromatography is the anti-pTau antibody with SEQ ID NO: 01 (heavy chain) and SEQ ID NO: 02 (light chain).

In one embodiment the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

In one embodiment the antibody is an antibody of the class IgG. In one embodiment the antibody is an antibody of the subclass IgG1, IgG2, IgG3 or IgG4. In one embodiment the antibody is an antibody of the subclass IgG1 or IgG4.

DETAILED DESCRIPTION OF EMBODIMENTS OF THE INVENTION

The invention is based, at least in part, on the finding that for the improvement of in vivo pharmacokinetic properties a defined increase of FcRn binding as determined by affinity chromatography on an FcRn affinity column is advantageous.

The combination of FcRn affinity chromatography and heparin affinity chromatography allows to define FcRn and heparin affinity chromatography column retention time thresholds and thereby a retention time region, wherein antibodies with slow clearance, i.e. long systemic circulation half-live, can be found. When the retention times on an FcRn affinity chromatography column and on a heparin affinity chromatography column are normalized based on the retention times of reference antibodies on the respective columns a relative retention time region comprising predominantly antibodies with slow clearance is defined. This region is defined by a relative retention time on the FcRn affinity chromatography column of less than 1.78 (with an anti-Her3 antibody as reference antibody) and by a relative retention time on the heparin affinity chromatography column of less than 0.87 (with an anti-pTau antibody as reference antibody).

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, MD (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, MD (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

The knobs into holes dimerization modules and their use in antibody engineering are described in Carter P.; Ridgway J. B. B.; Presta L. G.: Immunotechnology, Volume 2, Number 1, February 1996, pp. 73-73 (1).

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

It must be noted that as used herein and in the appended claims, the singular forms "a", "an", and "the" include plural reference unless the context clearly dictates otherwise. Thus, for example, reference to "a cell" includes one cell, a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "determine" as used herein encompasses also the terms measure and analyze.

The term "comprising" also includes the term "consisting of".

The term "antibody" herein is used in a broad sense and encompasses various antibody structures, including but not limited to monoclonal full length antibodies and multispecific antibodies (e.g. bispecific antibodies, trispecific antibodies) so long as they have an Fc-region.

A "multispecific antibody" denotes an antibody that has binding specificities for at least two different epitopes on the same antigen or two different antigens. Multispecific antibodies can be prepared as full-length antibodies or antibody fragments (e.g. F(ab')2 bispecific antibodies) or combinations thereof (e.g. full length antibody plus additional scFv or Fab fragments). Engineered antibodies with two, three or more (e.g. four) functional antigen binding sites have also been reported (see, e.g., US 2002/0004587 A1).

The term "binding (to an antigen)" denotes the binding of an antibody in an in vitro assay. In one embodiment binding is determined in a binding assay in which the antibody is bound to a surface and binding of the antigen to the antibody is measured by Surface Plasmon Resonance (SPR). Binding means e.g. a binding affinity ($K_D$) of $10^{-8}$ M or less, in some embodiments of $10^{-13}$ to $10^{-8}$ M, in some embodiments of $10^{-13}$ to $10^{-9}$ M. The term "binding" also includes the term "specifically binding".

Binding can be investigated by a BIAcore assay (GE Healthcare Biosensor AB, Uppsala, Sweden). The affinity of the binding is defined by the terms $k_a$ (rate constant for the association of the antibody from the antibody/antigen complex), $k_d$ (dissociation constant), and $K_D$ ($k_d/k_a$).

The term "buffer substance" denotes a substance that when in solution can level changes of the pH value of the solution e.g. due to the addition or release of acidic or basic substances.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

The term "Fc-fusion polypeptide" denotes a fusion of a binding domain (e.g. an antigen binding domain such as a single chain antibody, or a polypeptide such as a ligand of a receptor) with an antibody Fc-region.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 05. However, the C-terminal lysine (Lys447) of the Fc-region may or may not be present. The Fc-region is composed of two heavy chain Fc-region polypeptides, which can be covalently linked to each other via the hinge region cysteine residues forming inter-chain disulfide bonds.

The term "FcRn" denotes the human neonatal Fc-receptor. FcRn functions to salvage IgG from the lysosomal degradation pathway, resulting in reduced clearance and increased half-life. The FcRn is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of IgG. The interaction between IgG and FcRn is strictly pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440. In one embodiment one or more of the following amino acid residues according to the EU numbering of Kabat are altered F243, P244, P245, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, 1336, S337, K338, A339, K340, G341, Q342, P343, R344, E345, P346, Q347, V348, C367, V369, F372, Y373, P374, S375, D376, 1377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

The term "full length antibody" denotes an antibody having a structure substantially similar to a native antibody structure. A full length antibody comprises two full length antibody light chains comprising a light chain variable domain and a light chain constant domain and two full length antibody heavy chains comprising a heavy chain variable domain, a first constant domain, a hinge region, a second constant domain and a third constant domain. A full length antibody may comprise further domains, such as e.g. additional scFv or a scFab conjugated to one or more of the chains of the full length antibody. These conjugates are also encompassed by the term full length antibody.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "derived from" denotes that an amino acid sequence is derived from a parent amino acid sequence by introducing alterations at at least one position. Thus a derived amino acid sequence differs from the corresponding parent amino acid sequence at at least one corresponding position (numbering according to Kabat EU index for antibody Fc-regions). In one embodiment an amino acid sequence derived from a parent amino acid sequence differs by one to fifteen amino acid residues at corresponding positions. In one embodiment an amino acid sequence derived from a parent amino acid sequence differs by one to ten amino acid residues at corresponding positions. In one embodiment an amino acid sequence derived from a parent amino acid sequence differs by one to six amino acid residues at corresponding positions. Likewise, a derived amino acid sequence has a high amino acid sequence identity to its parent amino acid sequence. In one embodiment an amino acid sequence derived from a parent amino acid sequence has 80% or more amino acid sequence identity. In one embodiment an amino acid sequence derived from a parent amino acid sequence has 90% or more amino acid sequence identity. In one embodiment an amino acid sequence derived from a parent amino acid sequence has 95% or more amino acid sequence identity.

The term "human Fc-region polypeptide" denotes an amino acid sequence which is identical to a "native" or "wild-type" human Fc-region polypeptide. The term "variant (human) Fc-region polypeptide" denotes an amino acid sequence which derived from a "native" or "wild-type" human Fc-region polypeptide by virtue of at least one "amino acid alteration". A "human Fc-region" is consisting of two human Fc-region polypeptides. A "variant (human) Fc-region" is consisting of two Fc-region polypeptides, whereby both can be variant (human) Fc-region polypeptides or one is a human Fc-region polypeptide and the other is a variant (human) Fc-region polypeptide.

In one embodiment the human Fc-region polypeptide has the amino acid sequence of a human IgG1 Fc-region polypeptide of SEQ ID NO: 05, or of a human IgG2 Fc-region polypeptide of SEQ ID NO: 06, or of a human IgG3 Fc-region polypeptide of SEQ ID NO: 07, or of a human IgG4 Fc-region polypeptide of SEQ ID NO: 08. In one embodiment the Fc-region polypeptide is derived from an Fc-region polypeptide of SEQ ID NO: 05, or 06, or 07, or 08 and has at least one amino acid mutation compared to the Fc-region polypeptide of SEQ ID NO: 05, or 06, or 07, or 08. In one embodiment the Fc-region polypeptide comprises/has from about one to about ten amino acid mutations, and in one embodiment from about one to about five amino acid mutations. In one embodiment the Fc-region polypeptide has at least about 80% homology with a human Fc-region polypeptide of SEQ ID NO: 05, or 06, or 07, or 08. In one embodiment the Fc-region polypeptide has least about 90% homology with a human Fc-region polypeptide of SEQ ID NO: 05, or 06, or 07, or 08. In one embodiment the Fc-region polypeptide has at least about 95% homology with a human Fc-region polypeptide of SEQ ID NO: 05, or 06, or 07, or 08.

The Fc-region polypeptide derived from a human Fc-region polypeptide of SEQ ID NO: 05, or 06 or 07, or 08 is further defined by the amino acid alterations that are contained. Thus, for example, the term P329G denotes an Fc-region polypeptide derived human Fc-region polypeptide with the mutation of proline to glycine at amino acid position 329 relative to the human Fc-region polypeptide of SEQ ID NO: 05, or 06, or 07, or 08.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., size exclusion chromatography or ion exchange or reverse phase HPLC). For review of methods for assessment of antibody purity, see, e.g., Flatman, S. et al., J. Chrom. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "plasmid", as used herein, refers to a nucleic acid molecule capable of propagating another nucleic acid to which it is linked. The term includes the plasmid as a self-replicating nucleic acid structure as well as the plasmid incorporated into the genome of a host cell into which it has been introduced. Certain plasmids are capable of directing the expression of nucleic acids to which they are operatively linked. Such plasmids are referred to herein as "expression plasmid".

The term "positive linear pH gradient" denotes a pH gradient starting at a low (i.e. more acidic) pH value and ending at a higher (i.e. less acidic, neutral or alkaline) pH value. In one embodiment the positive linear pH gradient starts at a pH value of about 5.5 and ends at a pH value of about 8.8.

The term "recombinant antibody", as used herein, denotes all antibodies (chimeric, humanized and human) that are prepared, expressed, created or isolated by recombinant means. This includes antibodies isolated from a host cell such as a NS0, HEK, BHK or CHO cell or from an animal (e.g. a mouse) that is transgenic for human immunoglobulin genes or antibodies expressed using a recombinant expression plasmid transfected into a host cell. Such recombinant antibodies have variable and constant regions in a rearranged form. The recombinant antibodies as reported herein can be subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces in that a "solid support" contains at least one moiety on its surface, which is intended to interact chemically with a molecule. A solid phase may be a stationary component, such as a chip, tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, May 1 (1998) 322A-327A, which is incorporated herein by reference. In one embodiment the solid support is sepharose.

The term "valent" as used within the current application denotes the presence of a specified number of binding sites in a (antibody) molecule. As such, the terms "bivalent", "tetravalent", and "hexavalent" denote the presence of two binding site, four binding sites, and six binding sites, respectively, in a (antibody) molecule. The bispecific antibodies as reported herein as reported herein are in one preferred embodiment "bivalent".

The term "variable region" or "variable domain" refer to the domain of an antibody heavy or light chain that is involved in binding of the antibody to its antigen. The variable domains of the heavy chain and light chain (VH and VL, respectively) of an antibody generally have similar structures, with each domain comprising four framework regions (FRs) and three hypervariable regions (HVRs) (see, e.g., Kindt, T. J. et al. Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The terms "variant", "modified antibody", and "modified fusion polypeptide" denotes molecules which have an amino acid sequence that differs from the amino acid sequence of a parent molecule. Typically, such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent antibody or parent fusion polypeptide. In one embodiment the modified antibody or the variant fusion polypeptide has an amino acid sequence that has from about 75% to less than 100% amino acid sequence identity with the amino acid sequence of the parent antibody or parent fusion polypeptide, especially from about 80% to less than 100%, especially from about 85% to less than 100%, especially from about 90% to less than 100%, and especially from about 95% to less than 100%. In one embodiment the parent antibody or the parent fusion polypeptide and the modified antibody or the variant fusion polypeptide differ by one (a single), two or three amino acid residue(s).

II. Exemplary Embodiments of the Invention

The clearances of antibodies with identical Fc-region span a wide range. Also there is an influence of the respective Fv region, i.e. which biophysical properties differentiate fast cleared from slowly cleared antibodies.

Without being bound by this theory it is hypothesized that direct, charge-mediated interaction of Fv and FcRn impairs the release of the antibody from the FcRn at pH 7.4.

The combination of pinocytosis and FcRn binding evaluation can be used to characterize the pharmacokinetics of an antibody. This can be realized by the combination of FcRn affinity chromatography (pH-gradient elution) and heparin affinity chromatography (salt-gradient elution).

An intravenous immunoglobulin (IVIG, a polyclonal mix of IgGs isolated from pooled human donor serum (>1000 donors)) was separated on a heparin affinity chromatography column giving rise to several broad peaks covering a wide retention time range. The same material showed a narrow elution peak on the FcRn column suggesting similar binding affinities for FcRn for the therein contained antibodies (see FIG. 4).

Heparin is a highly negatively charged glycosaminoglycan (polysaccharide) and a main component of the glycocalix covering endothelial cells.

The fraction with the highest (FIG. 4: 2) and the lowest (FIG. 4: 1) heparin retention time was tested in FcRn wild-type and FcRn knock-out mice. The observed clearance is shown in the following Table:

| clearance [mL/day/kg] | FcRn-wt mice | FcRn-knock-out mice |
|---|---|---|
| IVIG heparin fraction 1 | 4 | 32 |
| IVIG heparin fraction 2 | 5 | 76 |

Higher clearance was found for the strong heparin binder, indicating a higher pinocytosis rate, in both settings.

In the mouse model expressing murine FcRn, which has a significantly higher affinity to huIgG compared to endogenous mIgG, FcRn recycling dominates the pharmacokinetic (without being bound by this theory there is strongly reduced competition of endogenous mIgG with the injected huIgG compared to the scenario in a patient). In FcRn knockout mice FcRn recycling does not contribute to pharmacokinetics and every pinocytosis event leads to the degradation of the pinocytosed IgG. Therefore, the thereby determined clearance should be proportionate to the pinocytosis rate of the injected IgG sample, resulting in a significantly more pronounced clearance. These data correlate well with the prediction of the heparin column, thereby adding evidence to the validity of the heparin column as predictor for antibody pharmacokinetics via pinocytosis.

The following 35 antibodies having different formats and different specificities have been produced and analyzed:

| antibody no | format | Fc-region | antigen no. |
|---|---|---|---|
| 1 | IgG1, bivalent, monospecific, reference heparin | LALAPG | 1 |
| 2 | IgG1, bivalent, monospecific | wild-type | 2 |
| 3 | IgG1, bivalent, monospecific | wild-type | 3 |
| 4 | CrossMab, bivalent, bispecific | KIH | 4 + 5 |
| 5 | IgG1, bivalent, monospecific | wild-type | 6 |
| 6 | IgG1, bivalent, monospecific | wild-type | 7 |
| 7 | IgG1, bivalent, monospecific | wild-type | 8 |
| 8 | IgG1, bivalent, monospecific | wild-type | 9 |
| 9 | IgG1, bivalent, monospecific | wild-type | 10 |
| 10 | IgG1, bivalent, monospecific, reference FcRn | wild-type | 11 |
| 11 | IgG1, bivalent, monospecific | wild-type | 12 |
| 12 | IgG4, bivalent, monospecific | wild-type | 13 |
| 13 | IgG1, bivalent, monospecific | wild-type | 9 |
| 14 | IgG1, bivalent, monospecific | wild-type | 14 |
| 15 | IgG1, bivalent, monospecific | wild-type | 15 |
| 16 | Fc-region-cytokine fusion | LALAPG | 16 |
| 17 | 2:1 heterodimeric T cell bispecific | KiH | 17 + 18 |
| 18 | 2:1 heterodimeric T cell bispecific | KIH | 9 + 18 |
| 19 | IgG1, bivalent, monospecific - cytokine fusion | KIH LALAPG | 16 + 19 |
| 20 | IgG1, bivalent, monospecific - cytokine fusion | KIH LALAPG | 16 + 17 |
| 21 | IgG1, bivalent, monospecific | wild-type | 20 + 21 |
| 22 | IgG1, bivalent, monospecific | wild-type | 20 + 21 |
| 23 | IgG1, bivalent, monospecific | wild-type | 22 |
| 24 | IgG1, bivalent, monospecific | wild-type | 23 |
| 25 | IgG1, bivalent, monospecific | wild-type | 24 |
| 26 | IgG1, bivalent, monospecific | wild-type | 25 |
| 27 | IgG1, bivalent, monospecific | wild-type | 26 |
| 28 | IgG1, bivalent, monospecific | wild-type | 27 |
| 29 | IgG1, bivalent, monospecific | wild-type | 28 |
| 30 | 2:1 heterodimeric T cell bispecific | KIH LALAPG | 29 + 18 |
| 31 | IgG1, bivalent, monospecific | wild-type | 9 |
| 32 | 2:1 heterodimeric T cell bispecific | KIH LALAPG | 17 + 18 |
| 33 | IgG1, bivalent, monospecific | LALAPG | 9 |
| 34 | IgG1-Fab fusion, trivalent, bispecific | KIH LALAPG | 9 + 30 |
| 35 | IgG1, bivalent, monospecific | wild-type | 31 |

A bivalent, monospecific IgG1 antibody with a wild-type-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains. In one embodiment the human IgG1 Fc-region has the amino acid sequence of SEQ ID NO: 05.

A bivalent, bispecific IgG1 antibody with a KiH-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains, whereby one of the heavy chain comprises the hole mutations and the respective other heavy chain comprises the knob mutation. In one embodiment the heavy chain Fc-regions have the amino acid sequence of SEQ ID NO: 09 and 10, respectively.

The CH3 domains in the Fc-reign of the heavy chains of a bivalent bispecific antibody can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

The mutation T366W in the CH3 domain of an antibody heavy chain is denoted as "knob mutation" and the mutations T366S, L368A, Y407V in the CH3 domain of an antibody heavy chain are denoted as "hole mutations" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the heavy chain with the "knob mutation" and by introducing a E356C mutation or a S354C mutation into the CH3 domain of the heavy chain with the "hole mutations", or vice versa.

A bivalent, monospecific IgG1 antibody cytokine fusion with a KiH LALAPG-Fc-region is an antibody comprising two antibody light chains (each comprising a light chain variable domain and a light chain constant domain) and two antibody heavy chains (each comprising a heavy chain variable domain, a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation, whereby both heavy chains further comprise the amino acid mutations L234A, L235A and P329G. In one embodiment the heavy chain Fc-regions have the amino acid sequence of SEQ ID NO: 18 and 19, respectively.

A bivalent, bispecific CrossMab with a KiH-Fc-region is an antibody comprising a) a first light chain and a first heavy chain of an antibody specifically binding to a first antigen, and a second light chain and a second heavy chain of an antibody specifically binding to a second antigen, wherein the variable domains VL and VH of the second light chain and the second heavy chain are replaced by each other, or b) a first light chain and a first heavy chain of an antibody specifically binding to a first antigen, and a second light chain and a second heavy chain of an antibody specifically binding to a second antigen, wherein the constant domains CL and CHI of the second light chain and the second heavy chain are replaced by each other, whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation. In one embodiment the heavy chain Fc-regions have the amino acid sequence of SEQ ID NO: 09 and 10, respectively.

A 2:1 heterodimeric T cell bispecific antibody with a KiH-LALAPG-Fc-region is an antibody comprising a) a first Fab fragment which specifically binds to a first antigen;

b) a second Fab fragment which specifically binds to a second antigen, and wherein the variable domains VL and VH or the constant domains CL and CH1 of the Fab light chain and the Fab heavy chain are replaced by each other;

c) a third Fab fragment which specifically binds to the first antigen; and d) an Fc-region composed of a first and a second heavy chain Fc-region;

wherein (iii) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the heavy chain Fc-regions under d), whereby the Fc-region is a human IgG1 Fc-region, whereby the Fc-region C-terminal amino acid residues K or GK may be present or not independently of each other in the two antibody heavy chain Fc-regions, whereby one of the heavy chain Fc-regions comprises the hole mutations and the respective other heavy chain Fc-region comprises the knob mutation, whereby both heavy chain Fc-regions further comprise the amino acid mutations L234A, L235A and P329G. In one embodiment the heavy chain Fc-regions have the amino acid sequence of SEQ ID NO: 18 and 19, respectively.

A trivalent, bispecific IgG1-Fab fusion with KiH-LALAPG-Fc-region comprises a) two light chains and two heavy chains of an antibody, which specifically bind to a first antigen (and comprise two Fab fragments), b) one additional Fab fragment of an antibody, which specifically binds to a second antigen, wherein said additional Fab fragment is fused via a peptidic linker to the C-terminus of one of the heavy chains of a), wherein in the additional Fab fragment either the variable domains VL and VH are replaced by each other, and/or the constant domains CL and CHI are replaced by each other, whereby the Fc-region is a human IgG1 Fc-region, whereby the Fc-region C-terminal amino acid residues K or GK may be present or not independently of each other in the two antibody heavy chains, whereby one of the heavy chains comprises the hole mutations and the respective other heavy chain comprises the knob mutation, whereby both heavy chains further comprise the amino acid mutations L234A, L235A and P329G. In one embodiment the heavy chain Fc-regions have the amino acid sequence of SEQ ID NO: 18 and 19, respectively.

An Fc-region-cytokine fusion with a LALAPG-Fc-region is an antibody Fc-region fusion comprising two antibody heavy chain Fc-region fragments (each comprising at least a fragment of a hinge region and the heavy chain constant domains CH1, CH2 and CH3), whereby the Fc-region is a human IgG1 Fc-region, whereby the Fc-region C-terminal amino acid residues K or GK may be present or not independently of each other in the two antibody heavy chain Fc-region fragments, whereby both antibody heavy chain Fc-region fragments comprise the amino acid mutations L234A, L235A and P329G. In one embodiment the heavy chain Fc-regions have the amino acid sequence of SEQ ID NO: 15.

In order to level intraday, intrapersonal and intra-laboratory variations the retention times are normalized to a reference antibody on each of the affinity columns.

For the heparin affinity chromatography column, the anti-pTau antibody with heavy chains of SEQ ID NO: 01 and light chains of SEQ ID NO: 02 was chosen. This antibody shows a relatively long retention time on the heparin affinity chromatography column resulting in a robust relative retention time calculation. For the FcRn affinity chromatography column a preparation comprising oxidized variants of the anti-Her 3 antibody with heavy chains of SEQ ID NO: 03 and light chains of SEQ ID NO: 04 was chosen. This antibody was chosen as it has a comparable AUC distribution as the antibody used in Stracke, J., et al. (mAbs 6 (2014) 1229-1242). For the 35 antibodies the retention times on an FcRn affinity chromatography column and a heparin affinity chromatography column have been determined. In addition, single-dose pharmacokinetics have been determined in cynomolgus monkeys. The results are presented in the following Table (same antibody sequence as before).

| antibody no | heparin affinity column rel. retention (vs. pTau) | FcRn affinity column rel. retention (vs. Her3 Pre-peak 1 and Main Peak) | clearance* [mL/kg/day] |
|---|---|---|---|
| 1 | 1 | 0.9 | 61.1 |
| 2 | 1.01 | 3.92 | 5.01 |
| 3 | 0.72 | 0.61 | 3.34 |
| 4 | 0.59 | 0.88 | 3.97 |
| 5 | 0.67 | 0.36 | 3.47 |
| 6 | 0.61 | 0.59 | 5.13 |
| 7 | 0.64 | 0.22 | 6.41 |
| 8 | 0.56 | 2.52 | 4.1 |
| 9 | 0.66 | 0.4 | 5.28 |
| 10 | 0.66 | 1.03 | 4.1 |
| 11 | 0.67 | 0.43 | 5.52 |
| 12 | 0.63 | -0.22 | 1.6 |
| 13 | 0.65 | 1.21 | <8 |
| 14 | 0.44 | 0.29 | 4.73 |
| 15 | 0.26 | -0.46 | 2.4 |
| 16 | 1.05 | 0.52 | >12 |
| 17 | 1 | 1.42 | 24.9 |
| 18 | 0.8 | 3.29 | 90 |
| 19 | 0.99 | 0.78 | 17 |
| 20 | 1.09 | 1.39 | 16.4 |
| 21 | 0.9 | 3.36 | >8 |
| 22 | 0.66 | 0.39 | >8 |
| 23 | 0.53 | 0.61 | 5.37 |
| 24 | 0.13 | −0.199 | 2.5 |
| 25 | 1.01 | 1.78 | 8.16 |
| 26 | 0.26 | −0.16 | 4.81 |
| 27 | 0.53 | 0.37 | 2.45 |
| 28 | 0.59 | 0.17 | 4.8 |
| 29 | 0.52 | 2.43 | 4.87 |
| 30 | 0.79 | 0.58 | 6.3 |
| 31 | 0.55 | 2.24 | 31.92 |
| 32 | 0.77 | 0.42 | 7.5 |
| 33 | 0.52 | 1.91 | 10.08 |
| 34 | 0.55 | 1.86 | 31.92 |
| 35 | 0.84 | 0.01 | 4.63 |

The clearance is ranked as follows:
fast: > 12 mL/kg/day;
borderline: 8-12 mL/kg/day;
acceptable: 2.5 ≤ X < 8 mL/kg/day;
very good: < 2.5 mL/kg/day.

The correlation of retention times and pharmacokinetic behavior is shown in FIG. 2. It can be seen that a correlation between relative retention times on the two affinity chromatography columns and pharmacokinetic behavior is existing. It has been found that a region comprising predominantly antibodies with slow clearance is defined by a relative retention time on the FcRn affinity chromatography column of less than 1.78 (with an anti-Her3 antibody as reference antibody) and by a relative retention time on the heparin affinity chromatography column of less than 0.87 (with an anti-pTau antibody as reference antibody). The respective correlation with the threshold values marked is shown in FIG. 3.

In one embodiment the reference antibody is an oxidized antibody preparation. In one embodiment the oxidized antibody preparation is a preparation comprising the antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono\text{-}oxidized\ peak}}{t_{reference\ antibody\ non\text{-}oxidized\ peak} - t_{reference\ antibody\ mono\text{-}oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04. In one embodiment the first threshold value is 2. In one embodiment the first threshold value is 1.8. In one embodiment the first threshold value is 1.78.

In one embodiment the second reference antibody is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment an immobilized non-covalent complex of a neonatal Fc receptor (FcRn) and beta-2-microglobulin (b2m) is used as affinity chromatography ligand in the FcRn affinity chromatography with a positive linear pH gradient,

- wherein the non-covalent complex of a neonatal Fc receptor and beta-2-microglobulin is bound to a chromatography material and the non-covalent complex is conjugated to the solid phase via a specific binding pair,
- wherein the pH gradient is from a first pH value to a second pH value whereby the first pH value is from pH 3.5 to pH 6.4 and the second pH value is from pH 7.4 to pH 9.5, and
- wherein the non-covalent complex of a neonatal Fc receptor (FcRn) and beta-2-microglobulin (b2m) is mono-biotinylated and the solid phase is derivatized with streptavidin.

In one embodiment the pH gradient is from a first pH value to a second pH value whereby the first pH value is pH 5.5 and the second pH value is pH 8.8.

In one embodiment the antibody is binding to two antigens.

In one embodiment the FcRn affinity chromatography is performed with an FcRn affinity chromatography column comprising streptavidin sepharose conjugated to FcRn beta-2-microglobulin complex (3 mg complex/1 ml of sepharose) and that has a length of about 50 mm and internal diameter of about 4.6 mm. In one embodiment the FcRn affinity chromatography is performed as follows: i) 30 μg of sample is applied onto the FcRn affinity column equilibrated with 20 mM MES buffer supplemented with 140 mM NaCl, adjusted to pH 5.5; ii) washing the column for 10 minutes with a buffer comprising (v/v) 80% 20 mM MES buffer supplemented with 140 mM NaCl, adjusted to pH 5.5 and 20% 20 mM Tris/HCl, with 140 mM NaCl, adjusted to pH 8.8 at a flow rate of 0.5 mL/min; iii) eluting and measuring the retention time with a linear gradient from the buffer of step ii) to a buffer comprising (v/v) 30% 20 mM MES buffer supplemented with 140 mM NaCl, adjusted to pH 5.5 and 70% 20 mM Tris/HCl, with 140 mM NaCl, adjusted to pH 8.8 at a flow rate of 0.5 mL/min.

In one embodiment the oxidized anti-Her3 antibody preparation is obtained by incubation of the anti-Her3 antibody for 18 hours at room temperature with 0.02% hydrogen peroxide solution.

In one embodiment the heparin affinity chromatography is performed with a heparin affinity chromatography column comprising heparin conjugated to sulfated glycosaminoglycan on a hydroxylated methacrylic polymer and that has a length of about 50 mm and in internal diameter of about 5 mm. In one embodiment the heparin affinity chromatography is performed as follows: i) applying 20 to 50 μg of protein samples in low-salt buffer (≤25 mM ionic strength) to a heparin affinity chromatography column pre-equilibrated with 50 mM TRIS buffer adjusted to pH 7.4 at room temperature; ii) eluting with a linear gradient from 0-100% 50 mM TRIS buffer supplemented with 1000 mM NaCl and adjusted to pH 7.4 over 32 minutes at a flow rate of 0.8 mg/mL.

In one embodiment the beta-2-microglobulin is from the same species as the FcRn.

The herein used FcRn affinity chromatography column comprises a matrix and matrix bound chromatographical functional groups, wherein the matrix bound chromatographical functional group comprises a non-covalent complex of neonatal Fc receptor (FcRn) and beta-2-microglobulin.

In one embodiment herein the FcRn is selected from human FcRn, cynomolgus FcRn, mouse FcRn, rat FcRn, sheep FcRn, dog FcRn, pig FcRn, minipig FcRn, and rabbit FcRn.

In one embodiment the beta-2-microglobulin is from the same species as the FcRn.

In one embodiment the beta-2-microglobulin is from a different species as the FcRn.

In one embodiment the antibody is selected from the group consisting of a full length antibody, a CrossMab or domain exchanged antibody, a 2:1 heterodimeric T cell bispecific antibody, an antibody-cytokine fusion polypeptide, an Fc-region-cytokine fusion polypeptide, and an antibody-Fab fusion polypeptide.

In one embodiment the antibody comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

In one embodiment the antibody format is selected from the group consisting of a full length antibody, a CrossMab, a 2:1 heterodimeric T cell bispecific antibody, and any of the before fused to one, two, or three additional Fab, scFv, scFab, CrossFab molecules either directly or via a peptidic linker.

In one embodiment the antibody format comprises an Fc-region selected from the group consisting of a human IgG1 Fc-region, a human IgG1 Fc-region with the mutations L234A, L235A and P329G, a human IgG1 Fc-region with the knob-into-hole mutations, and combinations thereof.

In one embodiment the antibody is a monoclonal antibody.

In one embodiment the antibody is a bispecific antibody.

In one embodiment the antibody is a chimeric antibody.

In general, the soluble extracellular domain of FcRn (SEQ ID NO: 31 for human FcRn) with C-terminal His-Avi Tag (SEQ ID NO: 32) was co-expressed with β2-microglobulin (SEQ ID NO: 33 for human beta-2-microglobulin) in mammalian cells. The non-covalent FcRn-microglobulin complex was biotinylated and loaded onto streptavidin derivatized sepharose.

To further elucidate the relation of charge and heparin/FcRn-binding and thereby pharmacokinetics, variants of antibody no. 5 were synthesized covering the biophysical space of charges and hydrophobicities normally seen in antibody Fvs.

Variants carrying positively charged patches showed strong heparin and FcRn column retention (relative retention of the FcRn column of 0.5 and more and relative retention on the heparin column of 0.8 or more), which predicts fast clearance.

Variants carrying negatively charged patches showed weak heparin and FcRn column retention (relative retention of the FcRn column of 0.25 and less and relative retention on the heparin column of 0.6 or less), which predicts slow clearance.

When combining negatively and positively charged patches, the resulting antibody variant behaves as if it was carrying only positively charged patches.

For the wild-type antibody no. 5 and four variants thereof the clearance in FcRn knock-out mice was determined (FIGS. 5 and 6). All three tested variants carrying positively charged patches show very high clearance compared to the wild-type antibody no. 5 in FcRn knock-out mice, correlating well with the column retentions. The variant carrying a negatively charged patch shows significantly reduced clearance in this mouse model also correlating well with the column retentions.

In order to determine the effect of "patchiness" on clearance (i.e. the effect of the concentration of surface charges to form a charge patch in contrast to an even charge distribution) five variants of antibody no. 5 were generated wherein the total number of positive and negative charges remained unchanged while the distribution of the charges on the Fab surface was incrementally changed from "even" to "patchy".

Although, both positive and negative charged patches were created, the heparin column retention increased with increasing patchiness. This indicates a bigger or even dominant effect of the positively charged patches compared to the negatively charged ones as already seen above. The calculated pI of these variants is nearly unchanged while the clearance in FcRn knock-out mice of the patchiest variant is significantly higher than that with the most even charge distribution (almost doubled; FIG. 7). These data suggest, without being bound by this theory, that "patchiness" or rather the influence of positively charged patches determines clearance in comparison to the pI which is a rather broad and therefore poor predictor of pharmacokinetics.

In order to determine the effect of replacing the permanently positively charged amino acids lysine and arginine with pH-dependently charged histidine a variant of antibody no. 5 in which all HC Fv positively charged amino acid residues were replaced with histidines (7 changes in total) was generated. This was compared by the heparin and FcRn column relative retention times and in vivo pharmacokinetic with the wild-type antibody no. 5.

Without being bound by this theory it is assumed that in blood serum at neutral pH, the charge of histidine is mostly neutral, therefore reducing binding to the negatively charged glycocalix and subsequently the pinocytosis rate. Within the acidic endosome histidine is mostly positive charged and therefore contributes to the binding to FcRn via Fv-FcRn avidity. Being recycled, the histidine mutated IgG is brought to the cell surface where efficient dissociation from FcRn is required for good pharmacokinetic. Histidines that are now exposed to the neutral pH of the serum become deprotonated and therefore weaken the avidity interaction with FcRn allowing for improved release to the serum.

The histidine mutant showed reduced heparin retention, whereas FcRn retention remains mostly unaltered (FIG. 8). Without being bound by this theory, this reflects the pH-dependency.

In vivo, clearance of the histidine mutant is significantly reduced compared to wild-type antibody in the FcRn knock-out mouse (FIGS. 9 and 10).

In one embodiment the modified antibody has at least one additional negatively charged patch on its (solvent-exposed) surface.

To determine charged patches on the (solvent exposed) surface of an antibody different methods and tools are known to a person skilled in the art. There are tools provided by different vendors or academic groups. For example, herein an in-silico calculation method based on the X-ray structure or a homology model, followed by pH-protonation of acidic and basic amino acid side-chains and calculation of the 3D charge distribution using the software CHARMM and Delphi as implemented in the software suite Discovery Studio (vendor: Dassault Systems) was used.

In one embodiment the modified antibody has at least one additional positively charged patch on its (solvent-exposed) surface.

In one embodiment the modified antibody has the same (surface) net charge as the parent antibody.

In one embodiment a (permanently) negatively charged amino acid residue is selected from the group consisting of glutamate and aspartate.

In one embodiment a (permanently) positively charged amino acid residue is selected from the group consisting of arginine and lysine.

In one embodiment the pH-dependently charged amino acid residue is histidine.

In one embodiment a permanently charged amino acid residue has the same (net) charge in the pH range from pH 6 to pH 8.

In one embodiment a pH-dependently charged amino acid residue has a first (net) charge at pH 6 and an opposite second (net) charge at pH 8.

In both FcRn-ko (knock-out) and hFcRn-tg (transgenic) mice, mAbs containing pos. charged patches showed fast clearance. In FcRn mice, mAbs that were engineered to carry more neg. charge patches, evenly distributed charges or His instead of Arg or Lys (pos. charged residues, even at neutral pH) showed slower clearance (red) compared to wild-type mAb. mAbs that were engineered to carry more pos. charge patches showed faster clearance (blue) compared to wild-type mAb (FIG. 11).

By calculating a ratio of clearance (ko/tg mice) an in vivo metric for FcRn recycling efficiency has been found. When plotting this ratio against the clearance in FcRn-ko mice (which correlates with charge patches and pinocytosis rate) large differences between various IgGs can be identified. When plotting the clearance in FcRn-ko mice against the ratio of clearance in FcRn-ko mice to hFcRn-tg mice a bell shaped curve is obtained (FIG. 12).

Binding of IgGs to FcRn occurs via two IgG domains: the canonical, specific FcRn binding site on the Fc domain and the a non-specific binding via the Fv domain, thereby creating avidity. Without being bound by this theory it is hypothesized that the molecules on the left side of FIG. 12 (low FcRn recycling efficiency and low pinocytosis rate) show reduced binding at pH 6 to FcRn due to the absence of pos. charge patches on the Fv domain and thereby have a reduced rate of being sorted into recycling endosomes but are degraded in the lysosome. In contrast molecules on the right side of FIG. 12 show reduced recycling efficiency due to their strong, Fv charge mediated interaction with FcRn at physiological pH and have therefore a lower dissociation rate at the cell surface. Antibodies with high recycling efficiency can be found in the peak of the curve as shown in FIG. 12.

Thus, the introduction of Fc-region mutations to increase FcRn affinity should improve the pharmacokinetic properties of antibodies by raising FcRn recycling efficiency (increased binding, important at pH 6.0) and should shift antibodies from the left side of FIG. 12 into the peak area.

Different variants of a parent antibody have been generated and characterized in vivo in human FcRn transgenic mice (hFcRn Tg32).

| Selection (x = in vivo PK) | | | | | | |
|---|---|---|---|---|---|---|
| | Fv variant | | | | | |
| Fc variant | v104 (even charge distribution) | v20 (negative patch) | v2 (his mutant) | v1 (parent antibody) | v108 (increased patchiness) | v27 (positive patch) |
| AAA(I253A, H310A, H435A) | | | | | | |
| Y436A | | | | | | x |
| WT | x | x | x | x | x | x |
| M428L | | x | | | | |
| T307H/N434H | | x | | | | |
| YTE (M252Y, S254T, T256E) | x | x | x | x | x | x |
| H433K/N434F | | x | | | | |

| variant | FcRn rel. Retention [min] (-wt) | CL (ml/kg/day) Tg32 hFcRn +/+ mice | fold CL change (to WT) in Tg32 hFcRn +/+ |
|---|---|---|---|
| 1-WT | 0 | 5.26 | 1 |
| 1-YTE | 3.72 | 3.69 | 0.70 |
| 104-WT | 0 | 3.67 | 1 |
| 104-YTE | 3.6 | 3.28 | 0.89 |
| 108-WT | 0 | 5.26 | 1 |
| 108-YTE | 3.63 | 4.53 | 0.86 |
| 2-WT | 0 | 3.63 | 1 |
| 2-YTE | 3.64 | 2.72 | 0.75 |
| 20-WT | 0 | 4.02 | 1 |
| 20-H433K/N434F | 7.74 | 6.46 | 1.61 |
| 20-M428L | 1.52 | 2.9 | 0.72 |
| 20-T307H/N434H | 3.75 | 3.21 | 0.8 |
| 20-YTE | 3.48 | 3.03 | 0.75 |
| 27-WT | 0 | 30.1 | 1 |

-continued

| variant | FcRn rel. Retention [min] (-wt) | CL (ml/kg/day) Tg32 hFcRn +/+ mice | fold CL change (to WT) in Tg32 hFcRn +/+ |
|---|---|---|---|
| 27-Y436A | −0.95 | 30.8 | 1.02 |
| 27-YTE | 4.87 | 18.2 | 0.60 |

The data contained in the table above is presented in FIG. 13 in an aligned plot, wherein on the y-axis the ratio of 'clearance in hFcRn+/+Tg32 mice of Fc-mutated variant' to 'clearance in hFcRn+/+Tg32 mice of corresponding parent (=wild-type) antibody' and wherein on the X-axis the difference of 'FcRn column rel. retention of Fc-mutated variant' and 'FcRn column rel. retention of corresponding parent (=wild-type) antibody' is depicted.

It can be seen that most variants shown a reduced clearance (Y-axis value below 1).

Mutation Y436A results in a reduced FcRn binding and thus, as expected the clearance is increased (Y-axis value above 1).

Mutations H433K/N434F results in a dramatically increased FcRn binding at pH 7.4 (X-axis value or more than 5, i.e. dissociation from FcRn at highly elevated pH value), which, as expected, results in an increased clearance (Y-axis value above 1) as dissociation of the antibody from FcRn at pH 7.4 is impaired and thereby FcRn-mediated recycling is reduced.

It can be seen from the data that a preferred "window" for the relative retention time change can be defined. This window spans the rime range of more than 1 minute to less than 5 minutes change of FcRn retention time relative to the respective parent antibody. Modification of the FcRn-binding in said "window" results for all variants in reduced clearance and thereby improved pharmacokinetic properties.

For 75% of the variants (6 out of 8) an even more narrow "window" of from more than 3 minutes to less than 4 minutes can be defined.

Thus, one aspect of the current invention is a method for providing an antibody with improved in vivo half-live, comprising the following steps:

a) determining the (relative) retention time of a (parent) antibody in an FcRn affinity chromatography,
b) modifying the Fc-region of the antibody by introducing mutations that increase the binding of the Fc-region to human FcRn to obtain a modified antibody,
c) determining the (relative) retention time of the modified antibody in an FcRn affinity chromatography, d) repeating step b) if the change of the relative retention time between the (parent) antibody and the modified antibody is less than about 1 minute and more than about 5 minutes, whereby in case the change of the relative retention time is less than 1 minute mutations are chosen that result in a further increased binding of the Fc-region to human FcRn or in case the change of the relative retention time is more than 5 minutes mutations are chosen that result in a less increased binding of the Fc-region to human FcRn, e) providing an antibody with improved in vivo half-live if the change of the relative retention time between the (parent) antibody and the modified antibody is more than about 1 minute and less than about 2 minutes.

In one embodiment the FcRn affinity chromatography is performed as follows:

an FcRn affinity chromatography column comprising about 1 mL of a streptavidin agarose matrix with human FcRn conjugated thereto via biotin-streptavidin non-covalent interaction (in one preferred embodiment with 1 mg to 5 mg FcRn per g matrix, preferably 2.5 mg FcRn per g matrix) is equilibrated with 80 vol-% buffer A (20 mM MES sodium salt, 140 mM NaCl, pH 5.5) and 20 vol-% buffer B (20 mM Tris/HCl, 140 mM NaCl, pH 8.8) at a flow rate of 0.5 mL/min and a column temperature of 25° C.;

a total of 30 μg of the antibody is prepared in the same mixture of 80 vol-% buffer A and 20 vol-% buffer B and injected on the equilibrated column;

ten minutes post injection, a linear gradient from 20 vol-% to 100 vol-% buffer B over 70 minutes is started;

optionally 100 vol-% buffer B is held for 10 minutes before the column is re-equilibrated with 80 vol-% buffer A and 20 vol-% buffer B;

whereby detection is performed with a UV detector set at 280 nm;

whereby (in order to make results from different runs and different buffer and column lots comparable, and to compensate for slight retention time drifts, a standard sample is measured at the beginning and the end of each sequence and after every $10^{th}$ run) a relative retention time on the FcRn affinity chromatography column is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak\ 2}$: retention time of peak 2 of the partially oxidized anti-Her3 antibody according to FIG. 1; $t_{peak\ 3}$: retention time of peak 3 of the anti-Her3 antibody according to FIG. 1).

In one embodiment the FcRn is a non-covalent complex with human beta-2-microglobulin (b2m).

In one embodiment the method comprises as step b) the following step:

b) modifying the Fc-region of the antibody by introducing mutations that increase the binding of the Fc-region to human FcRn to obtain a modified antibody,
and
modifying the Fv of the antibody by
reducing the size of positively charged patches,
reducing the size of positively charged patches and increasing the size of negatively charged patches,
making the overall distribution of charges in the Fv more even.

In one embodiment the charge distribution in the Fv fragment is changed by i) changing at least one (permanently) negatively charged or not charged amino acid residue to a (permanently) positively charged amino acid residue, or ii) changing at least one (permanently) positively charged or not charged amino acid residue to a (permanently) negatively charged amino acid residue, or iii) changing at least one (permanently) charged amino acid residue to an amino acid residue with the opposite charge, or iv) changing at least one permanently charged amino acid residue to a pH-dependently charged amino acid residue, or v) a combination of i) to iv).

When the retention times on an FcRn affinity chromatography column and on a heparin affinity chromatography column are normalized based on the retention times of reference antibodies on the respective columns, a relative retention time region comprising predominantly antibodies with slow clearance is defined. This region is defined by a relative retention time on the FcRn affinity chromatography column of less than 1.78 (with an oxidized (H2O2-treated) anti-Her3 antibody preparation as reference antibody) and by a relative retention time on the heparin affinity chromatography column of less than 0.87 (with an anti-pTau antibody as reference antibody).

In one embodiment the method further comprises the following steps:

e) performing an FcRn affinity chromatography with a positive linear pH gradient and a heparin affinity chromatography with a positive linear conductivity/salt gradient with the parent antibody and the modified antibody, and f) providing an antibody with improved in vivo half-live if the modified antibody has
   i) a relative retention time on the FcRn affinity chromatography column that is less than the retention time of the parent antibody on the (same) FcRn affinity chromatography column (under the same elution conditions), or
   ii) a relative retention time on the heparin affinity chromatography column that is less than the retention time of the parent antibody on the (same) heparin affinity chromatography column (under the same elution conditions), or
   iii) both of i) and ii).

In one embodiment the method further comprises the following steps:

e) performing an FcRn affinity chromatography with a positive linear pH gradient and a heparin affinity chromatography with a positive linear conductivity/salt gradient with the parent antibody and the modified antibody, and f) providing an antibody with improved in vivo half-live if the modified antibody has
   i) a relative retention time on the FcRn affinity chromatography column that is more than the retention time of the parent antibody on the (same) FcRn affinity chromatography column (under the same elution conditions), or ii) a relative retention time on the heparin affinity chromatography column that is more than the retention time of the parent antibody on the (same) heparin affinity chromatography column (under the same elution conditions), or iii) both of i) and ii).

In one embodiment the method further comprises the following steps:

e) performing an FcRn affinity chromatography with a positive linear pH gradient and a heparin affinity chromatography with a positive linear conductivity/salt gradient with the parent antibody and the modified antibody, and f) providing an antibody with improved in vivo half-live if the modified antibody has i) a relative retention time on the FcRn affinity chromatography column that is less or more than the retention time of the parent antibody on the (same) FcRn affinity chromatography column (under the same elution conditions), or ii) a relative retention time on the heparin affinity chromatography column that is less or more than the retention time of the parent antibody on the (same) heparin affinity chromatography column (under the same elution conditions), or iii) both of i) and ii), wherein in i) the relative retention time is less and ii) it is more, or vice versa.

To determine charged patches on the (solvent exposed) surface of an antibody different methods and tools are known to a person skilled in the art. There are tools provided by different vendors or academic groups. For example, herein an in-silico calculation method based on the X-ray structure or a homology model, followed by pH-protonation of acidic and basic amino acid side-chains and calculation of the 3D charge distribution using the software CHARMM and Delphi as implemented in the software suite Discovery Studio (vendor: Dassault Systems) was used.

In one embodiment the modified antibody has at least one additional negatively charged patch on its (solvent-exposed) surface.

In one embodiment the modified antibody has the same (surface) net charge as the parent antibody.

In one embodiment a (permanently) negatively charged amino acid residue is selected from the group consisting of glutamate and aspartate.

In one embodiment a (permanently) positively charged amino acid residue is selected from the group consisting of arginine and lysine.

In one embodiment the pH-dependently charged amino acid residue is histidine.

In one embodiment a permanently charged amino acid residue has the same (net) charge in the pH range from pH 6 to pH 8.

In one embodiment a pH-dependently charged amino acid residue has a first (net) charge at pH 6 and an opposite second (net) charge at pH 8.

In one embodiment the standard sample is an oxidized antibody preparation comprising the reference antibody with respect to the methionine residues at position 252 in the heavy chain CH2 domains in non-oxidized form, in mono-oxidized form (only one of the two methionins at position 252 is oxidized) and in bi-oxidized form (both methionine residues at position 252 are oxidized) (numbering according to Kabat). In one embodiment the relative retention time is calculated based on the following formula $$t_{rel,i} = \frac{t_i - t_{reference\ antibody\ mono-oxidized\ peak}}{t_{reference\ antibody\ non-oxidized\ peak} - t_{reference\ antibody\ mono-oxidized\ peak}}$$

with $t_{rel,i}$=relative retention time of the antibody; $t_i$=retention time of the antibody. In one embodiment the first reference antibody is an anti-Her3 antibody that has a heavy chain with the amino acid sequence of SEQ ID NO: 03 and a light chain with the amino acid sequence of SEQ ID NO: 04.

In one embodiment the first threshold value in step f) is 2. In one embodiment the first threshold value is 1.8. In one embodiment the first threshold value is 1.78.

In one embodiment the second reference antibody in step f) is an anti-pTau antibody that has a heavy chain with the amino acid sequence of SEQ ID NO: 01 and a light chain with the amino acid sequence of SEQ ID NO: 02. In one embodiment the second threshold value is 1. In one embodiment the second threshold value is 0.8. In one embodiment the second threshold value is 0.78.

In one embodiment step f) is providing an antibody with improved in vivo half-live if the modified antibody has i) a relative retention time on the FcRn affinity chromatography column is less than 1.78 times the retention time difference between peaks 2 and 3 of a preparation of an oxidized anti-Her3 antibody of SEQ ID NO: 03 and 04, and ii) a relative retention time on the heparin affinity chromatography column is less than 0.87 times the retention time of an anti-pTau antibody of SEQ ID NO: 01 and 02.

In one embodiment of all methods the relative retention time on the FcRn affinity chromatography column is calculated according to the following equation:

$$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak\ 2}$: retention time of peak 2 of the partially oxidized anti-Her3 antibody according to FIG. 1; $t_{peak\ 3}$: retention time of peak 3 of the anti-Her3 antibody according to FIG. 1).

In one embodiment of all methods the relative retention time on the heparin affinity chromatography column is calculated according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

In one embodiment in the FcRn affinity chromatography of step e) with a positive linear pH gradient is used an immobilized non-covalent complex of a neonatal Fc receptor (FcRn) and beta-2-microglobulin (b2m) as affinity chromatography ligand, wherein the non-covalent complex of a neonatal Fc receptor and beta-2-microglobulin is bound to a chromatography material and the non-covalent complex is conjugated to the solid phase via a specific binding pair, wherein the pH gradient is from a first pH value to a second pH value whereby the first pH value is from pH 3.5 to pH 6.4 and the second pH value is from pH 7.4 to pH 9.5, and wherein the non-covalent complex of a neonatal Fc receptor (FcRn) and beta-2-microglobulin (b2m) is mono-biotinylated and the solid phase is derivatized with streptavidin.

In one embodiment the pH gradient of step e) is from a first pH value to a second pH value whereby the first pH value is pH 5.5 and the second pH value is pH 8.8.

In one embodiment the beta-2-microglobulin is from the same species as the FcRn. In one embodiment the FcRn is selected from human FcRn, cynomolgus FcRn, mouse FcRn, rat FcRn, sheep FcRn, dog FcRn, pig FcRn, minipig FcRn, and rabbit FcRn.

In one embodiment the beta-2-microglobulin is from the same species as the FcRn.

In one embodiment the beta-2-microglobulin is from a different species as the FcRn.

In general, the soluble extracellular domain of FcRn (SEQ ID NO: 31 for human FcRn) with C-terminal His-Avi Tag (SEQ ID NO: 32) was co-expressed with $\beta_2$-microglobulin (SEQ ID NO: 33 for human beta-2-microglobulin) in mammalian cells. The non-covalent FcRn-microglobulin complex was biotinylated and loaded onto streptavidin derivatized sepharose.

In one embodiment the reference antibody for the FcRn affinity chromatography is the anti-HER3 antibody with SEQ ID NO: 03 (heavy chain) and SEQ ID NO: 04 (light chain).

In one embodiment the reference antibody for the heparin affinity chromatography is the anti-pTau antibody with SEQ ID NO: 01 (heavy chain) and SEQ ID NO: 02 (light chain).

In one embodiment the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

In one embodiment the antibody is an antibody of the class IgG. In one embodiment the antibody is an antibody of the subclass IgG1, IgG2, IgG3 or IgG4. In one embodiment the antibody is an antibody of the subclass IgG1 or IgG4.

III. The Neonatal Fc-Receptor (FcRn)

The neonatal Fc-receptor (FcRn) is important for the metabolic fate of antibodies of the IgG class in vivo. The FcRn functions to salvage wild-type IgG from the lysosomal degradation pathway, resulting in reduced clearance and increased half-life. It is a heterodimeric protein consisting of two polypeptides: a 50 kDa class I major histocompatibility complex-like protein (α-FcRn) and a 15 kDa β2-microglobulin (β2m). FcRn binds with high affinity to the CH2-CH3 portion of the Fc-region of an antibody of the class IgG. The interaction between an antibody of the class IgG and the FcRn is pH dependent and occurs in a 1:2 stoichiometry, i.e. one IgG antibody molecule can interact with two FcRn molecules via its two heavy chain Fc-region polypeptides (see e.g. Huber, A. H., et al., J. Mol. Biol. 230 (1993) 1077-1083).

Thus, an IgGs in vitro FcRn binding properties/characteristics are indicative of its in vivo pharmacokinetic properties in the blood circulation.

In the interaction between the FcRn and the Fc-region of an antibody of the IgG class different amino acid residues of the heavy chain CH2- and CH3-domain are participating. The amino acid residues interacting with the FcRn are located approximately between EU position 243 and EU position 261, approximately between EU position 275 and EU position 293, approximately between EU position 302 and EU position 319, approximately between EU position 336 and EU position 348, approximately between EU position 367 and EU position 393, at EU position 408, and approximately between EU position 424 and EU position 440. More specifically the following amino acid residues according to the EU numbering of Kabat are involved in the interaction between the Fc-region and the FcRn: F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440.

Site-directed mutagenesis studies have proven that the critical binding sites in the Fc-region of IgGs for FcRn are Histidine 310, Histidine 435, and Isoleucine 253 and to a lesser extent Histidine 433 and Tyrosine 436 (see e.g. Kim, J. K., et al., Eur. J. Immunol. 29 (1999) 2819-2825; Raghavan, M., et al., Biochem. 34 (1995) 14649-14657; Medesan, C., et al., J Immunol. 158 (1997) 2211-2217).

Methods to increase IgG binding to FcRn have been performed by mutating IgG at various amino acid residues: Threonine 250, Methionine 252, Serine 254, Threonine 256, Threonine 307, Glutamic acid 380, Methionine 428, Histidine 433, and Asparagine 434 (see Kuo, T. T., et al., J. Clin. Immunol. 30 (2010) 777-789).

In some cases, antibodies with reduced half-life in the blood circulation are desired. For example, drugs for intravitreal application should have a long half-live in the eye and a short half-life in the blood circulation of the patient. Such antibodies also have the advantage of increased exposure to a disease site, e.g. in the eye.

Different mutations that influence the FcRn binding and therewith the half-live in the blood circulation are known. Fc-region residues critical to the mouse Fc-region-mouse FcRn interaction have been identified by site-directed mutagenesis (see e.g. Dall'Acqua, W. F., et al. J. Immunol 169 (2002) 5171-5180). Residues I253, H310, H433, N434, and H435 (EU numbering according to Kabat) are involved in the interaction (Medesan, C., et al., Eur. J. Immunol. 26 (1996) 2533-2536; Firan, M., et al., Int. Immunol. 13 (2001) 993-1002; Kim, J. K., et al., Eur. J. Immunol. 24 (1994) 542-548). Residues I253, H310, and H435 were found to be critical for the interaction of human Fc with murine FcRn (Kim, J. K., et al., Eur. J. Immunol. 29 (1999) 2819-2855). Residues M252Y, S254T, T256E have been described by Dall'Acqua et al. to improve FcRn binding by protein-protein interaction studies (Dall'Acqua, W. F., et al. J. Biol. Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993-1002; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

Exemplary mutations and their effect on FcRn binding are listed in the following Table.

TABLE

| mutation | effect on FcRn binding | half-live in the circulation | reference |
|---|---|---|---|
| H285<br>H310Q/H433N<br>(murine IgG1) | reduced<br>(murine) | reduced<br>(in mouse) | Kim, J.K., Scand. J. Immunol. 40 (1994) 457-465 |
| I253A<br>H310A<br>H435A<br>H436A<br>(murine IgG1) | reduced<br>(murine) | reduced<br>(in mouse) | Ghetie, V. and Ward, E.S., Immunol. Today 18 (1997) 592-598 |
| T252L/T254S/T256F<br>T252A/T254S/T256A<br>(murine IgG1) | increased<br>(murine) | increased<br>(in mouse) | Ghetie, V. and Ward, E.S., Immunol. Today 18 (1997) 592-598 |
| I253A<br>H310A<br>H435A<br>H436A<br>H433A/N434Q<br>(murine IgG1) | reduced<br>(murine) | reduced<br>(in mouse) | Medesan, C., et al., J. Immunol. 158 (1997) 2211-2217 |
| I253A<br>H310A<br>H435A<br>H435R<br>(human IgG1) | reduced<br>H310A: <0.1 rel. binding to muFcRn<br>(murine) | reduced<br>(in mouse) | Kim, J.K., Eur. J. Immunol. 29 (1999) 2819-2825 |
| H433A<br>(human IgG1) | 1.1 rel. binding to muFcRn, 0.4 rel. binding hu FcRn<br>(murine) | | Kim, J.K., Eur. J. Immunol. 29 (1999) 2819-2825 |
| I253A<br>S254A<br>H435A<br>Y436A<br>(human IgG1) | reduced<br><0.1 relative binding to huFcRn | reduced | Shields, R.L., et al., J. Biol. Chem. 276 (2001) 6591-6604 |
| R255A<br>K288A<br>L309A<br>S415A<br>H433A<br>(human IgG1) | reduced<br>(human) | reduced | Shields, R.L., et al., J. Biol. Chem. 276 (2001) 6591-6604 |
| P238A<br>T256A<br>E272A<br>V305A<br>T307A<br>Q311A<br>D312A<br>K317A<br>D376A<br>A378Q<br>E380A<br>E382A<br>S424A<br>N434A<br>K288A/N434A<br>E380A/N434A<br>T307A/E380A/N434A<br>(human IgG1) | increased<br>(human) | increased | Shields, R.L., et al., J. Biol. Chem. 276 (2001) 6591-6604 |

TABLE-continued

| mutation | effect on FcRn binding | half-live in the circulation | reference |
|---|---|---|---|
| H435A<br>(humanized IgG1) | reduced<br><0.1 rel. binding to huFcRn | reduced | Firan, M., et al., Int. Immunol. 13 (2001) 993-1002 |
| I253A (no binding)<br>M252W<br>M252Y<br>M252Y/T256Q<br>M252F/T256D<br>N434F/Y436H<br>M252Y/S254T/T256E<br>G385A/Q386P/N389S<br>H433K/N434F/Y436H<br>H433R/N434Y/Y436H<br>G385R/Q386T/P387R/N389P<br>M252Y/S254T/T256E/KH433/N434F/Y436H<br>M252Y/S254T/T256E/G385R/Q386T/P387R/N389P<br>(human IgG1) | increased<br>(murine and human) | reduced<br>(in mouse) | Dall'Acqua, J. Immunol. 169 (2002) 5171-5180 |
| M428L<br>T250Q/M428L<br>(human IgG2) | increased<br>(human) | increased<br>(in monkey) | Hinton, P.R., et al., J. Biol. Chem. 279 (2004) 6213-6216 |
| M252Y/S254T/T256E +<br>H433K/N434F<br>(human IgG) | increased<br>(human) | increased<br>(in mouse) | Vaccaro, C., et al., Nat. Biotechnol. 23 (2005) 1283-1288 |
| T307A/E380A/N434A<br>(chimeric IgG1) | increased | increased in transgenic mouse | Pop, L.M., et al., Int. Immunopharmacol. 5 (2005) 1279-1290 |
| T250Q<br>E380A<br>M428L<br>N434A<br>K288A/N434A<br>E380A/N434A<br>T307A/E380A/N434A<br>(human IgG1) | increased<br>(human) | increased in transgenic mouse | Petkova, S.B., et al., Int. Immunol 18 (2006) 1759-1769 |
| I253A<br>(human IgG1) | reduced<br>(human) | reduced in transgenic mouse | Petkova, S.B., et al., Int. Immunol 18 (2006) 1759-1769 |
| S239D/A330L/I332E<br>M252Y/S254T/T256E<br>(humanized) | increased<br>(human and Cynomolgus) | increased in Cynomolgus | Dall'Acqua, W.F., et al., J. Biol. Chem. 281 (2006) 23514-23524 |
| T250Q<br>M428L<br>T250Q/M428L<br>(human IgG1) | increased<br>(human) | increased in Rhesus apes | Hinton, P.R., et al., J. Immunol. 176 (2006) 346-356 |
| T250Q/M428L<br>P257I/Q311I<br>(humanized IgG1) | increased<br>(mouse and Cynomolgus) | no change in Cynomolgus increased in mouse | Datta-Mannan, A., et al., J. Biol. Chem. 282 (2007) 1709-1717 |
| P257I/Q311I<br>P257I/N434H<br>D376V/N434H<br>(humanized IgG1) | increased at pH 6<br>(human, Cynomolgus, mouse) | reduced in mice<br>P257I/N434H reduced in Cynomolgus | Datta-Mannan, A., et al., Drug Metab. Dispos. 35 (2007) 86-94 |

TABLE-continued

| mutation | effect on FcRn binding | half-live in the circulation | reference |
|---|---|---|---|
| abrogate FcRn binding: I253 H310 H433 H435 reduce FcRn binding: Y436 increased FcRn binding: T250 N252 S254 T256 T307 M428 N434 | increased and reduced | reducing the binding ability of IgG for FcRn reduces its serum persistence; a higher-affinity FcRn-IgG interaction prolongs the half-lives of IgG and Fc-coupled drugs in the serum | Ropeenian, D.C. and Akilesh, S., Nat. Rev. Immunol. 7 (2007) 715-725 |
| N434A T307Q/N434A T307Q/N434S V308P/N434A T307Q/E380A/N434A (human IgG1) | increased (Cynomolgus monkey) | increased in Cynomolgus monkey | Yeung, Y.A., et al., Cancer Res. 70 (2010) 3269-3277 |
| 256P 280K 339T 385H 428L 434W/Y/F/A/H (human IgG) | increased at neutral pH | | WO 2011/122011 |

Figure 1:
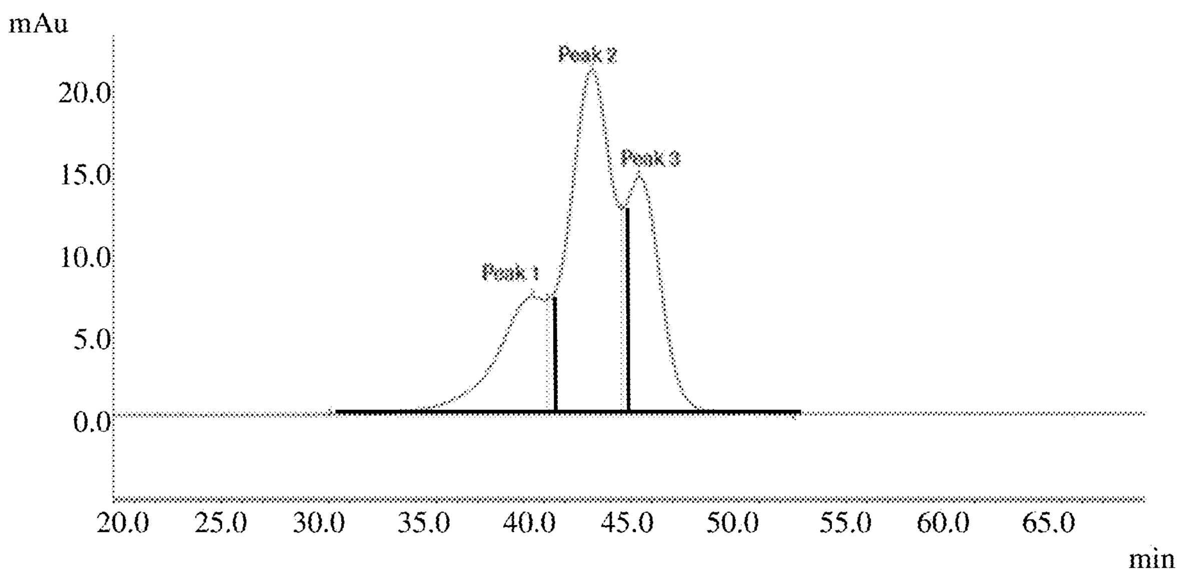
FIG. 1 Peak definition for the calculation of relative retention times on the FcRn column.
Figure 2:
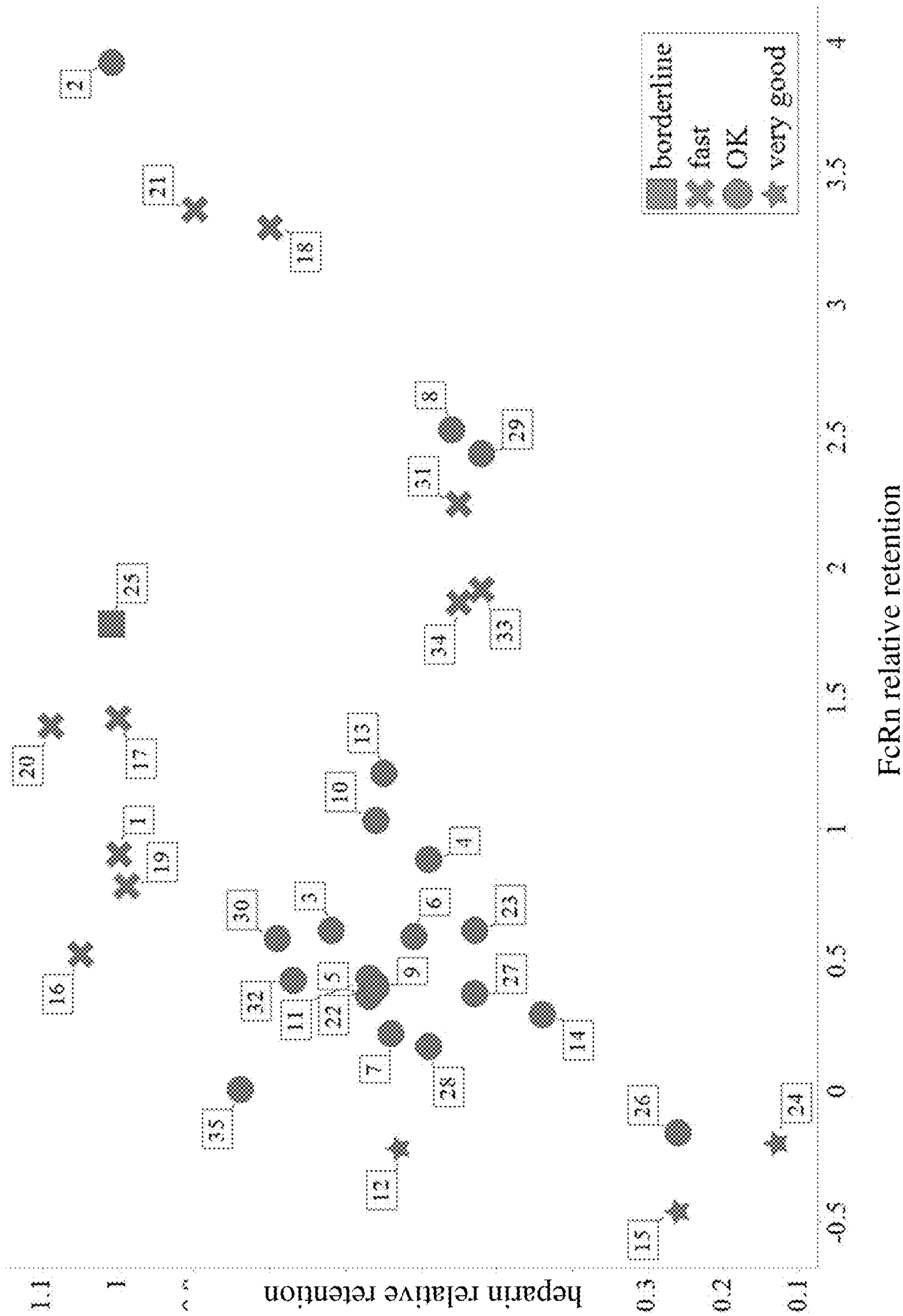
FIG. 2 FcRn relative retention plotted vs. heparin column relative retention. cross: clearance >12 mL/kg/day ("fast"); filled square: clearance between 8 and 12 mL/kg/day ("borderline"); filled circle: clearance more than 2.5 mL/kg/day but less than 8 mL/kg/day; filled star: clearance of 2.5 mL/kg/day or less.
Figure 3:
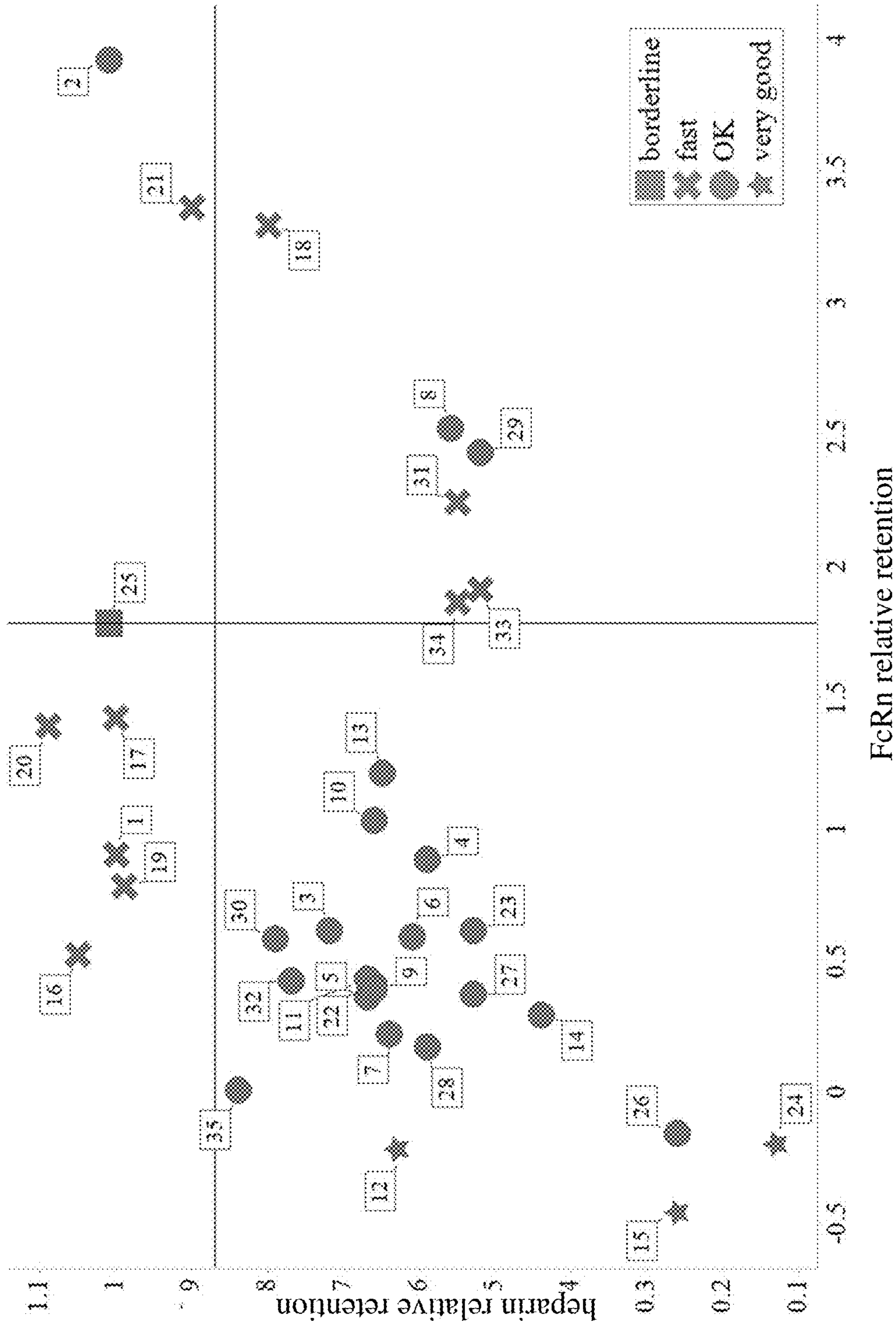
FIG. 3 FcRn relative retention plotted vs. heparin column relative retention. cross: clearance >12 mL/kg/day ("fast"); filled square: clearance between 8 and 12 mL/kg/day ("borderline"); filled circle: clearance more than 2.5 mL/kg/day but less than 8 mL/kg/day; filled star: clearance of 2.5 mL/kg/day or less; vertical lines mark the retention time ranges for therapeutically suitable clearance (lower-left quadrant, FcRn <1.78; Heparin: <0.87).
Figure 4:
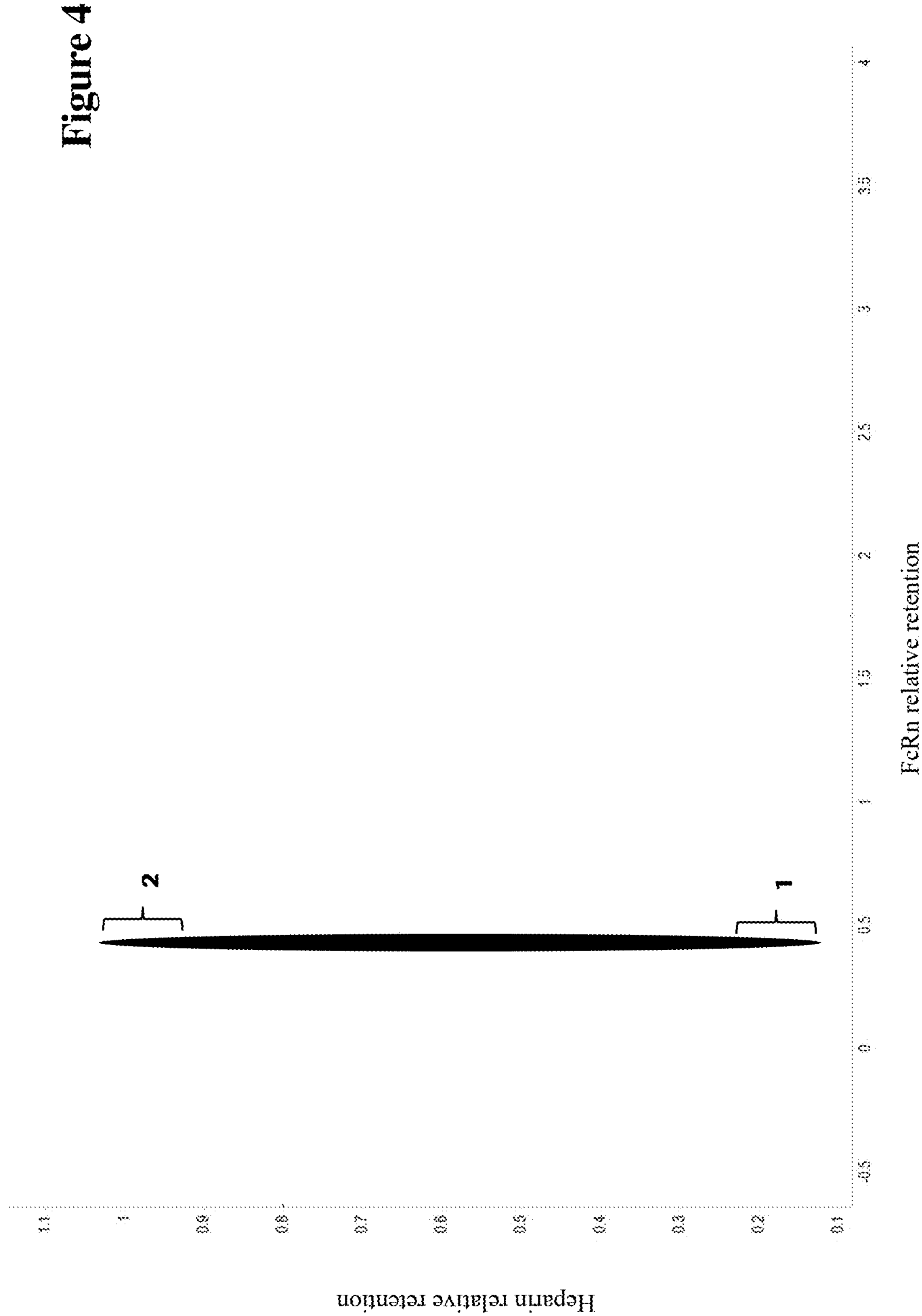
FIG. 4 FcRn relative retention plotted vs. heparin column relative retention of IVIG (intravenous immunoglobulin). 2: fraction with highest heparin binding; 1: fraction with lowest heparin binding.
Figure 5:
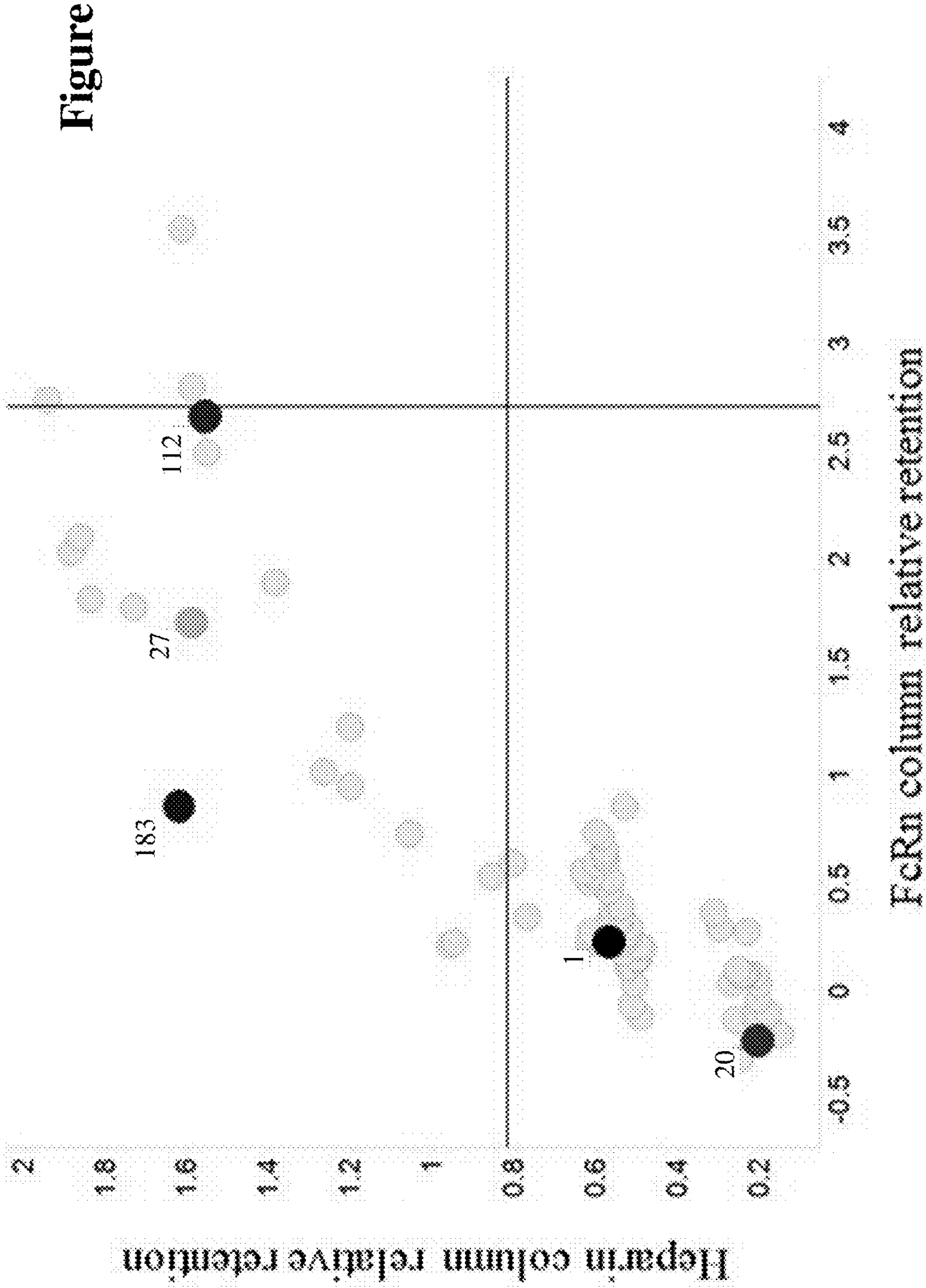
FIG. 5 FcRn relative retention plotted vs. heparin column relative retention of antibody no. 5 and variants thereof. 1: wild-type antibody; 20: negatively patched HC variant; 27: positively patched HC variant; 112: positively patched LC variant; 183: positively patched HC variant.
Figure 6:
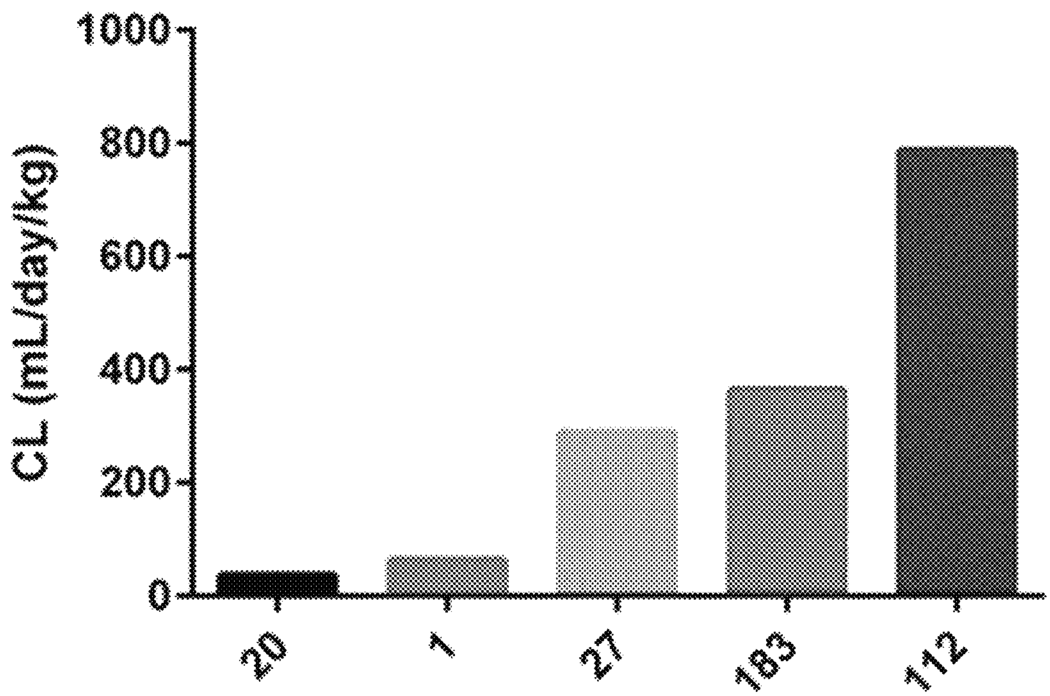
FIG. 6 Clearance of antibody no. 5 and variants thereof in FcRn knock-out mice. 1: wild-type antibody; 20: negatively patched HC variant; 27: positively patched HC variant; 112: positively patched LC variant; 183: positively patched HC variant.
Figure 7:
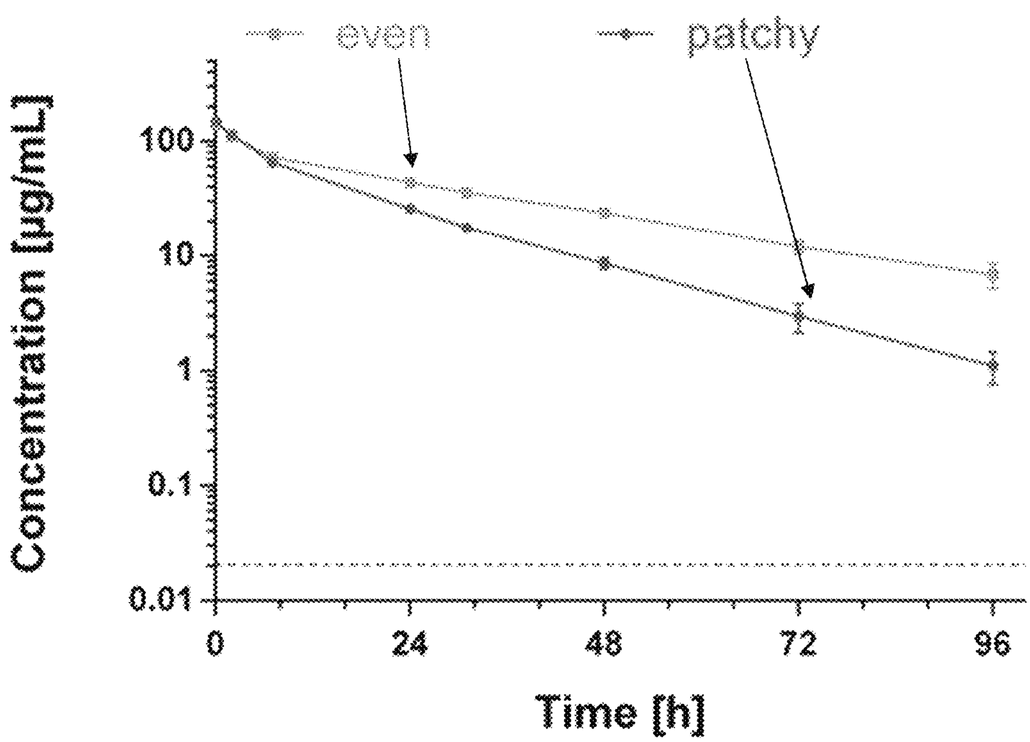
FIG. 7 Time dependent serum concentration of a non-patchy and a patchy variant of antibody no. 5 in FcRn knock-out mice.
Figure 8:
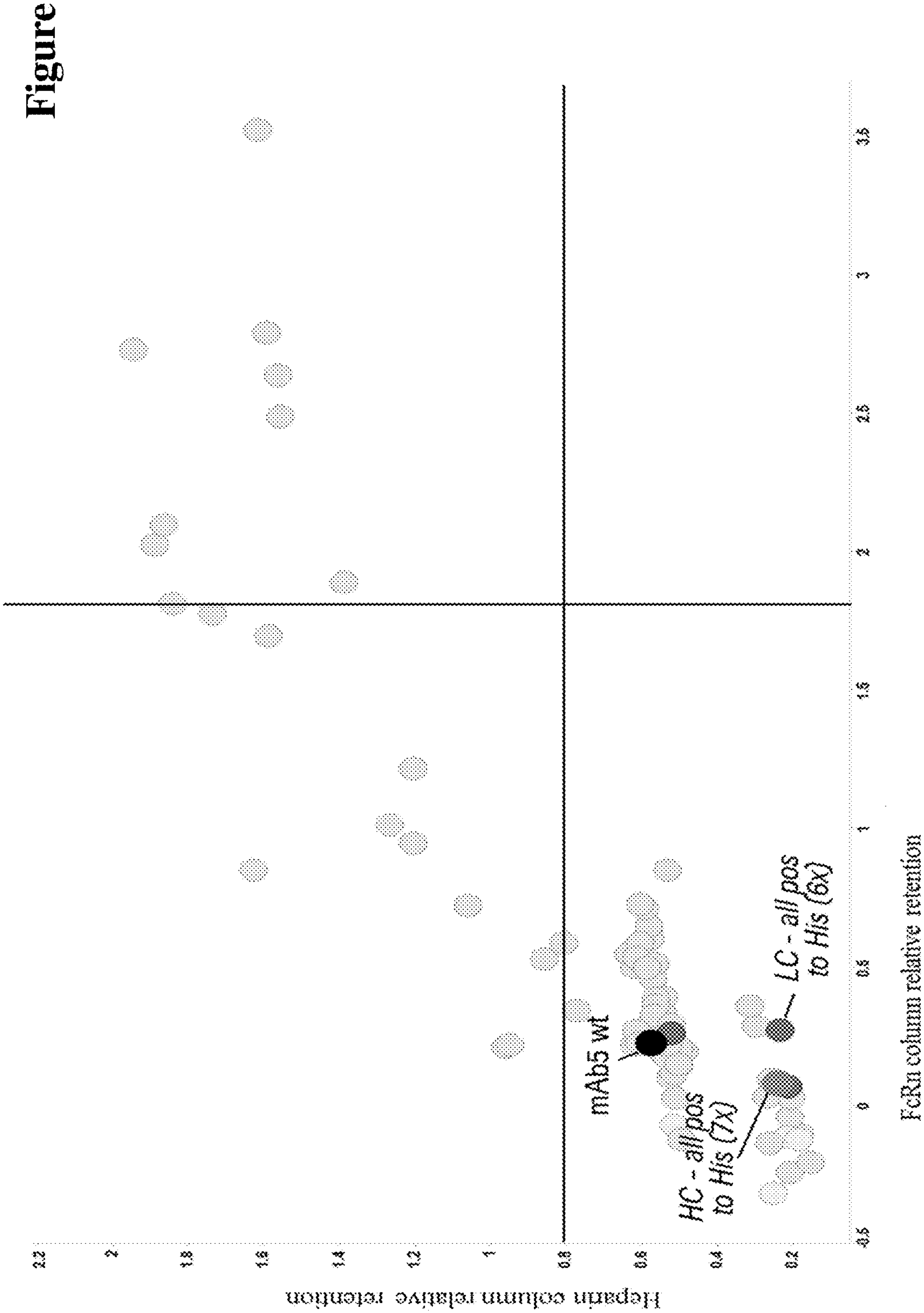
FIG. 8 FcRn relative retention plotted vs. heparin column relative retention of antibody no. 5 and histidine variants thereof.
Figure 9:
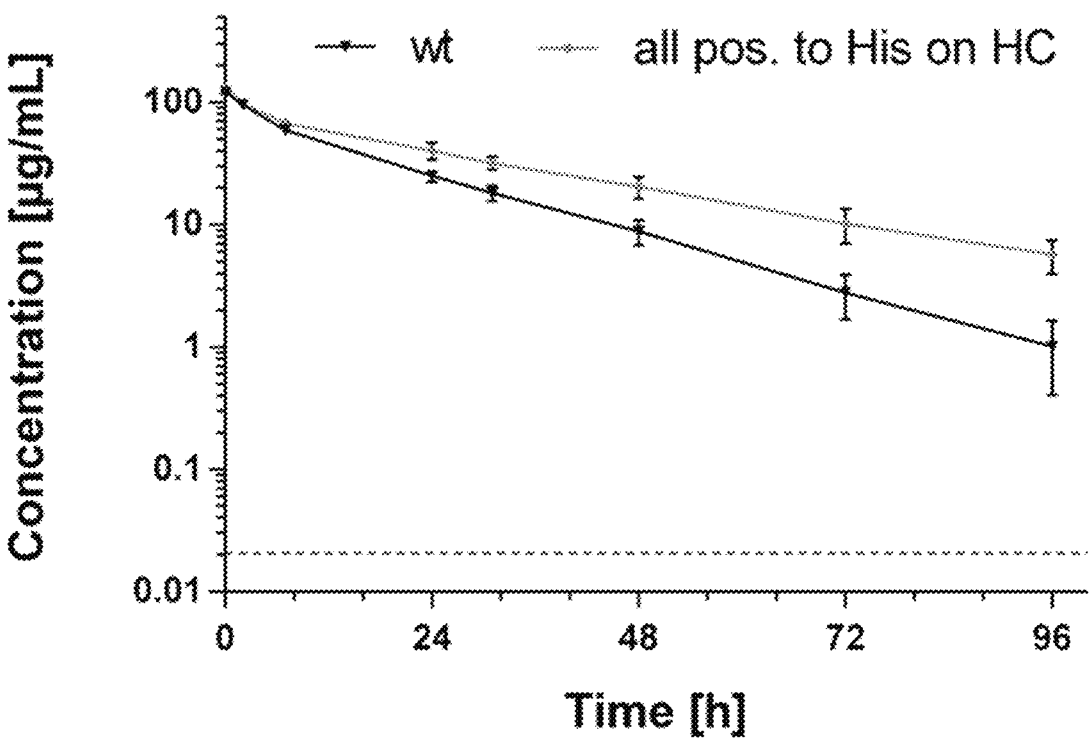
FIG. 9 Time dependent serum concentration of antibody no. 5 and a HC histidine variant thereof in FcRn knock-out mice.
Figure 10:
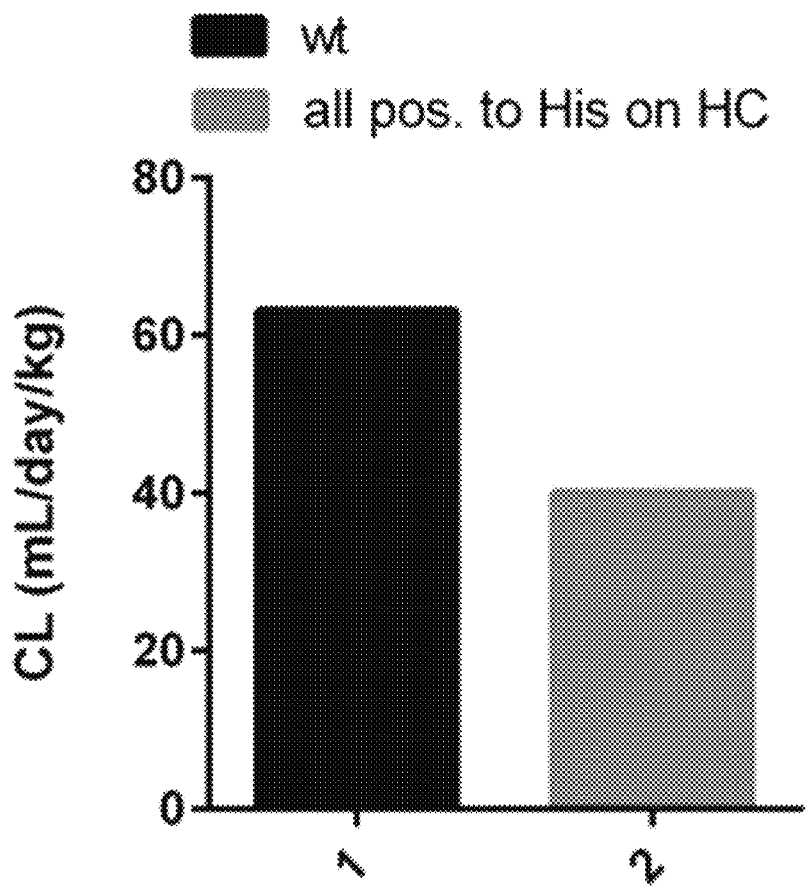
FIG. 10 Clearance of antibody no. 5 and a HC histidine variant thereof in FcRn knock-out mice.
Figure 11A:
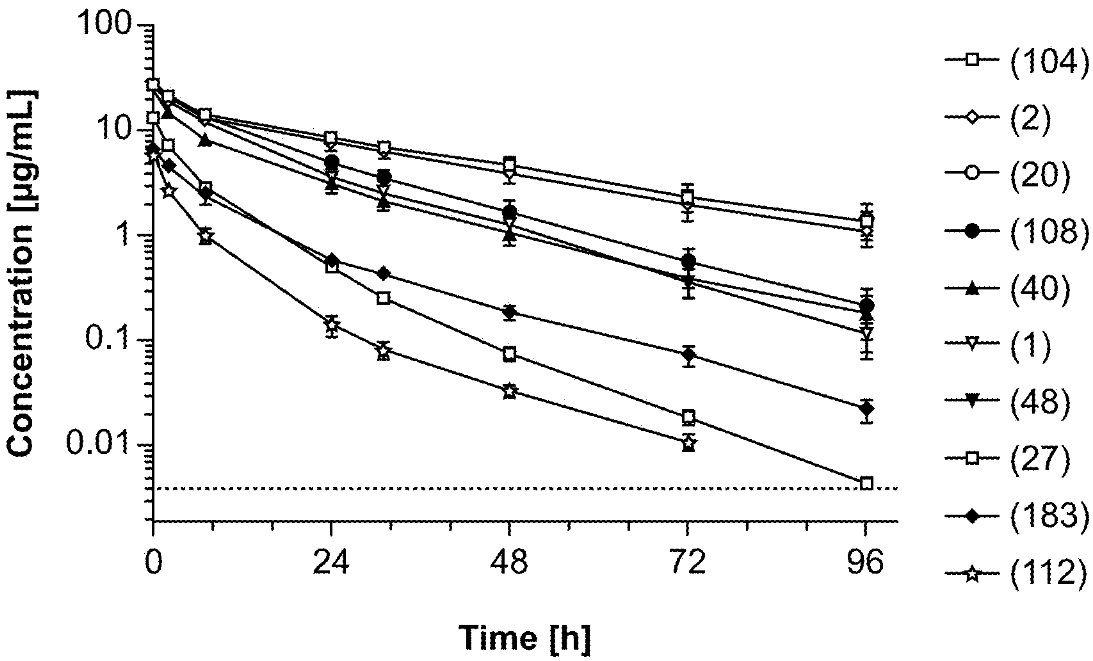
FIGS. 11A and 11B: Influence of Fv charge patches on FcRn recycling in hFcRn-tg (FIG. 11B) and FcRn-ko (FIG. 11A) mice; sequence symbols in the legend from top to bottom correspond to the sequence of the graphs from top to bottom at the sample point at about 2 hours and about 24 hours, respectively.
Figure 11B:
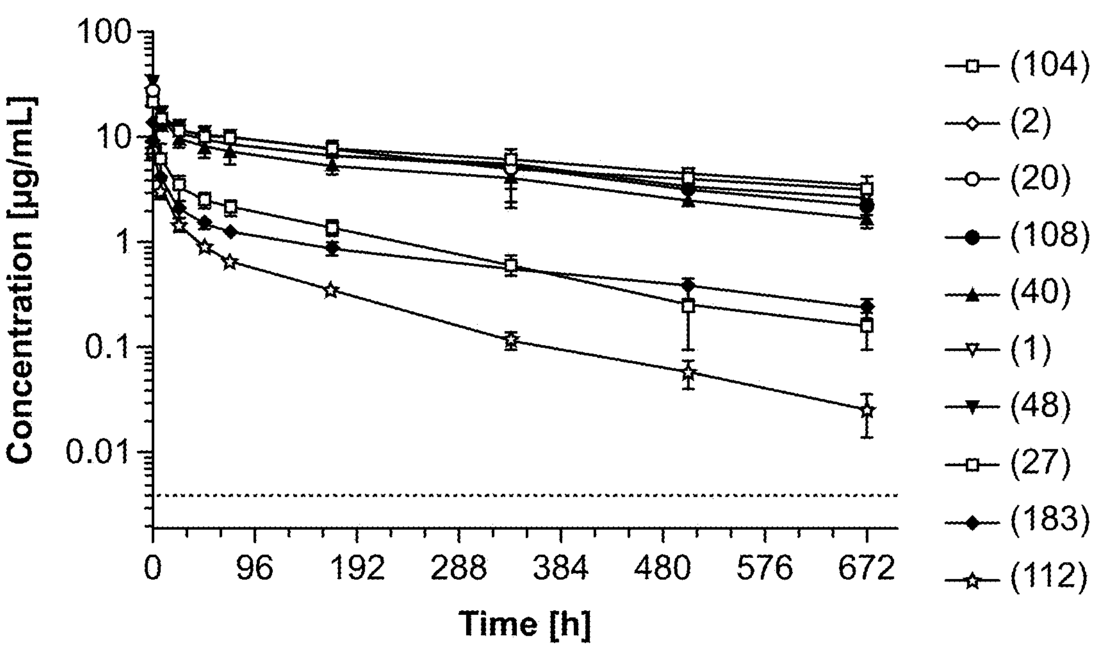
Figure 12:
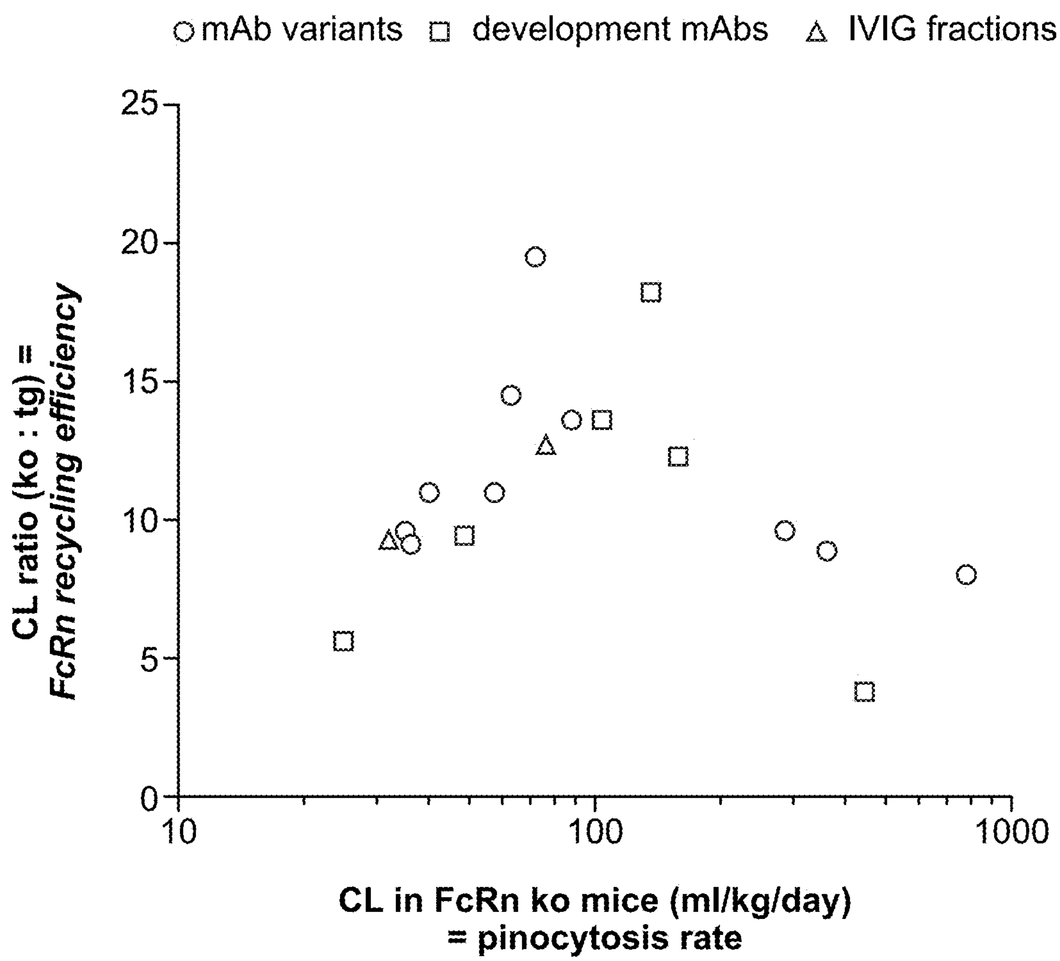
FIG. 12: Plot of the clearance in FcRn-ko mice against the ratio of clearance in FcRn-ko mice to hFcRn-tg mice for the variants of FIG. 11 (blue circles), some mAbs in development (red squares), and some IVIG fractions (green triangle).
Figure 13:
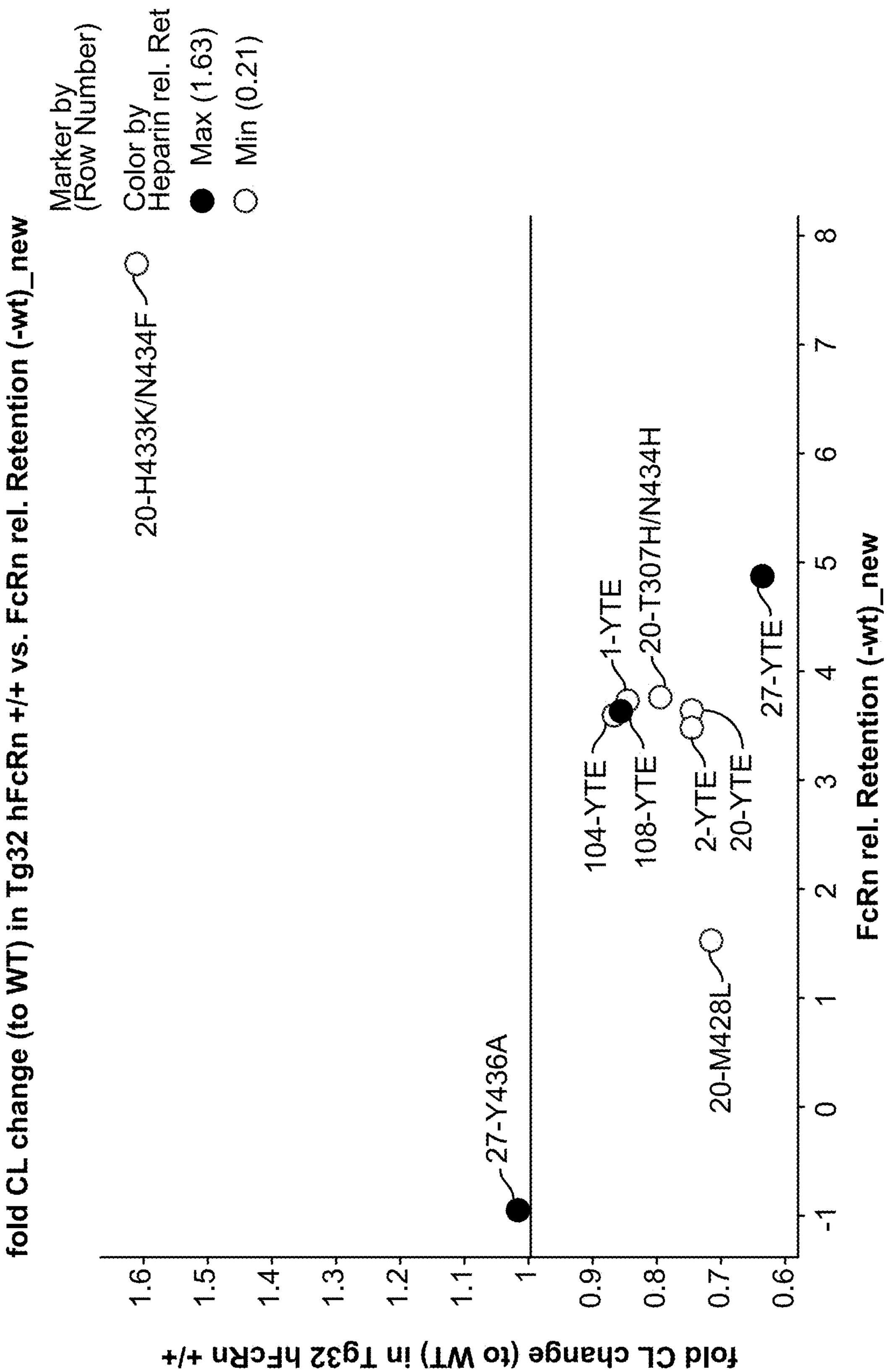
FIG. 13: Plot of the ratio of 'clearance in hFcRn+/+Tg32 mice of Fc-mutated variant' to 'clearance in hFcRn+/+Tg32 mice of corresponding parent (=wild-type) antibody' against the difference of 'FcRn column rel. retention of Fc-mutated variant' and 'FcRn column rel. retention of corresponding parent (=wild-type) antibody' of modified antibodies.

The following examples, figures and sequences are provided to aid the understanding of the present invention, the true scope of which is set forth in the appended claims. It is understood that modifications can be made in the procedures set forth without departing from the spirit of the invention.

Materials and Methods

Antibodies

The reference antibodies used in the experiments were an anti-pTau antibody that has the heavy chain amino acid sequence of SEQ ID NO: 01 and the light chain amino acid sequence of SEQ ID NO: 02 and an anti-Her 3 antibody that has the heavy chain amino acid sequence of SEQ ID NO: 03 and the light chain amino acid sequence of SEQ ID NO: 04.

Synthetic genes were produced at Geneart (Life technologies GmbH, Carlsbad, CA, USA).

The monoclonal antibodies used herein were transiently expressed in HEK293 cells (see below) and purification was performed by protein A chromatography using standard procedures (see below).

The biochemical characterization included size exclusion chromatography (Waters BioSuite™ 250 7.8×300 mm, eluent: 200 mM $KH_2PO_4$, 250 mM KCl, pH 7.0) and analysis of the molecular weight distribution using the BioAnalyzer 2100 (Agilent technologies, Santa Clara, CA, USA).

Expression Plasmids

For the expression of the above described antibodies, variants of expression plasmids for transient expression (e.g. in HEK293-F) cells based either on a cDNA organization with or without a CMV-Intron A promoter or on a genomic organization with a CMV promoter were applied.

Beside the antibody expression cassette, the plasmids contained:

- an origin of replication which allows replication of this plasmid in *E. coli,*
- a β-lactamase gene which confers ampicillin resistance in *E. coli*., and
- the dihydrofolate reductase gene from *Mus musculus* as a selectable marker in eukaryotic cells.

The transcription unit of the antibody gene was composed of the following elements:

- unique restriction site(s) at the 5' end
- the immediate early enhancer and promoter from the human cytomegalovirus, followed by the Intron A sequence in the case of the cDNA organization, a 5'-untranslated region of a human antibody gene, an immunoglobulin heavy chain signal sequence, the human antibody chain either as cDNA or as genomic organization with the immunoglobulin exon-intron organization a 3' non-translated region with a polyadenylation signal sequence, and unique restriction site(s) at the 3' end.

The fusion genes comprising the antibody chains were generated by PCR and/or gene synthesis and assembled by known recombinant methods and techniques by connection of the according nucleic acid segments e.g. using unique restriction sites in the respective plasmids. The subcloned nucleic acid sequences were verified by DNA sequencing. For transient transfections larger quantities of the plasmids were prepared by plasmid preparation from transformed *E. coli* cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System

The antibodies were generated by transient transfection with the respective plasmids (e.g. encoding the heavy chain, as well as the corresponding light chain) using the HEK293-F system (Invitrogen) according to the manufacturer's instruction. Briefly, HEK293-F cells (Invitrogen) growing in suspension either in a shake flask or in a stirred fermenter in serum-free FreeStyle™ 293 expression medium (Invitrogen) were transfected with a mix of the respective expression plasmids and 293fectin™ or fectin (Invitrogen). For 2 L shake flask (Corning) HEK293-F cells were seeded at a density of $1*10^6$ cells/mL in 600 mL and incubated at 120 rpm, 8% $CO_2$. The day after the cells were transfected at a cell density of ca. $1.5*10^6$ cells/mL with ca. 42 mL mix of A) 20 mL Opti-MEM (Invitrogen) with 600 µg total plasmid DNA (1 µg/mL) encoding the heavy chain, respectively and the corresponding light chain in an equimolar ratio and B) 20 ml Opti-MEM+1.2 mL 293 fectin or fectin (2 µL/mL). According to the glucose consumption glucose solution was added during the course of the fermentation. The supernatant containing the secreted antibody was harvested after 5-10 days and antibodies were either directly purified from the supernatant or the supernatant was frozen and stored. The following antibodies have been produced accordingly:

| antibody no | format | Fc-region | antigen no. |
|---|---|---|---|
| 1 | IgG1, bivalent, monospecific, reference heparin | LALAPG | 1 |
| 2 | IgG1, bivalent, monospecific | wild-type | 2 |
| 3 | IgG1, bivalent, monospecific | wild-type | 3 |
| 4 | CrossMab, bivalent, bispecific | KIH | 4 + 5 |
| 5 | IgG1, bivalent, monospecific | wild-type | 6 |
| 6 | IgG1, bivalent, monospecific | wild-type | 7 |
| 7 | IgG1, bivalent, monospecific | wild-type | 8 |
| 8 | IgG1, bivalent, monospecific | wild-type | 9 |
| 9 | IgG1, bivalent, monospecific | wild-type | 10 |
| 10 | IgG1, bivalent, monospecific, reference FcRn | wild-type | 11 |
| 11 | IgG1, bivalent, monospecific | wild-type | 12 |
| 12 | IgG4, bivalent, monospecific | wild-type | 13 |
| 13 | IgG1, bivalent, monospecific | wild-type | 9 |

-continued

| antibody no | format | Fc-region | antigen no. |
|---|---|---|---|
| 14 | IgG1, bivalent, monospecific | wild-type | 14 |
| 15 | IgG1, bivalent, monospecific | wild-type | 15 |
| 16 | Fc-region-cytokine fusion | LALAPG | 16 |
| 17 | 2:1 heterodimeric T cell bispecific | KIH | 17 + 18 |
| 18 | 2:1 heterodimeric T cell bispecific | KIH | 9 + 18 |
| 19 | IgG1, bivalent, monospecific - cytokine fusion | KIH LALAPG | 16 + 19 |
| 20 | IgG1, bivalent, monospecific - cytokine fusion | KIH LALAPG | 16 + 17 |
| 21 | IgG1, bivalent, monospecific | wild-type | 20 + 21 |
| 22 | IgG1, bivalent, monospecific | wild-type | 20 + 21 |
| 23 | IgG1, bivalent, monospecific | wild-type | 22 |
| 24 | IgG1, bivalent, monospecific | wild-type | 23 |
| 25 | IgG1, bivalent, monospecific | wild-type | 24 |
| 26 | IgG1, bivalent, monospecific | wild-type | 25 |
| 27 | IgG1, bivalent, monospecific | wild-type | 26 |
| 28 | IgG1, bivalent, monospecific | wild-type | 27 |
| 29 | IgG1, bivalent, monospecific | wild-type | 28 |
| 30 | 2:1 heterodimeric T cell bispecific | KIH LALAPG | 29 + 18 |
| 31 | IgG1, bivalent, monospecific | wild-type | 9 |
| 32 | 2:1 heterodimeric T cell bispecific | KIH LALAPG | 17 + 18 |
| 33 | IgG1, bivalent, monospecific | LALAPG | 9 |
| 34 | IgG1-Fab fusion, trivalent, bispecific | KIH LALAPG | 9 + 30 |
| 35 | IgG1, bivalent, monospecific | wild-type | 31 |

Purification

The antibodies were purified from cell culture supernatants by affinity chromatography using MabSelectSure-Sepharose™ (GE Healthcare, Sweden), hydrophobic interaction chromatography using butyl-Sepharose (GE Healthcare, Sweden) and Superdex 200 size exclusion (GE Healthcare, Sweden) chromatography.

Briefly, sterile filtered cell culture supernatants were captured on a MabSelectSuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted antibody fractions were pooled and neutralized with 2 M Tris, pH 9.0. The antibody pools were prepared for hydrophobic interaction chromatography by adding 1.6 M ammonium sulfate solution to a final concentration of 0.8 M ammonium sulfate and the pH adjusted to pH 5.0 using acetic acid. After equilibration of the butyl-Sepharose resin with 35 mM sodium acetate, 0.8 M ammonium sulfate, pH 5.0, the antibodies were applied to the resin, washed with equilibration buffer and eluted with a linear gradient to 35 mM sodium acetate pH 5.0. The antibody containing fractions were pooled and further purified by size exclusion chromatography using a Superdex 200 26/60 GL (GE Healthcare, Sweden) column equilibrated with 20 mM histidine, 140 mM NaCl, pH 6.0. The antibody containing fractions were pooled, concentrated to the required concentration using Vivaspin ultrafiltration devices (Sartorius Stedim Biotech S.A., France) and stored at −80° C.

Purity and antibody integrity were analyzed after each purification step by CE-SDS using microfluidic Labchip technology (Caliper Life Science, USA). Five µl of protein solution was prepared for CE-SDS analysis using the HT Protein Express Reagent Kit according manufacturer's instructions and analyzed on LabChip GXII system using a HT Protein Express Chip. Data were analyzed using LabChip GX Software.

Mice

B6.Cg-Fcgrt$^{tm1Dcr}$ Tg (FCGRT) 276Dcr mice deficient in mouse FcRn α-chain gene, but hemizygous transgenic for a human FcRn α-chain gene (muFcRn−/− huFcRn tg +/−, line 276) were used for the pharmacokinetic studies. Mouse husbandry was carried out under specific pathogen free conditions. Mice were obtained from the Jackson Laboratory (Bar Harbor, ME, USA) (female, age 4-10 weeks, weight 17-22 g at time of dosing). All animal experiments were approved by the Government of Upper Bavaria, Germany (permit number 55.2-1-54-2532.2-28-10) and performed in an AAALAC accredited animal facility according to the European Union Normative for Care and Use of Experimental Animals. The animals were housed in standard cages and had free access to food and water during the whole study period.

Pharmacokinetic Studies

A single dose of antibody was injected i.v. via the lateral tail vein at a dose level of 10 mg/kg. The mice were divided into 3 groups of 6 mice each to cover 9 serum collection time points in total (at 0.08, 2, 8, 24, 48, 168, 336, 504 and 672 hours post dose). Each mouse was subjected twice to retro-orbital bleeding, performed under light anesthesia with Isoflurane™ (CP-Pharma GmbH, Burgdorf, Germany); a third blood sample was collected at the time of euthanasia. Blood was collected into serum tubes (Microvette 500Z-Gel, Sarstedt, Nümbrecht, Germany). After 2 h incubation, samples were centrifuged for 3 min at 9.300 g to obtain serum. After centrifugation, serum samples were stored frozen at −20° C. until analysis.

Determination of Human Antibody Serum Concentrations

Concentrations of Ustekinumab, Briakinumab, mAb 8 and mAb 9 in murine serum were determined by specific enzyme-linked immunoassays. Biotinylated Interleukin 12 specific to the antibodies and digoxigenin-labeled anti-human-Fc mouse monoclonal antibody (Roche Diagnostics, Penzberg, Germany) were used for capturing and detection, respectively. Streptavidin-coated microtiter plates (Roche Diagnostics, Penzberg, Germany) were coated with biotinylated capture antibody diluted in assay buffer (Roche Diagnostics, Penzberg, Germany) for 1 h. After washing, serum samples were added at various dilutions followed by another incubation step for 1 h. After repeated washings, bound human antibodies were detected by subsequent incubation with detection antibody, followed by an anti-digoxigenin antibody conjugated to horseradish peroxidase (HRP; Roche Diagnostics, Penzberg, Germany). ABTS (2,2'Azino-di [3-ethylbenzthiazoline sulfonate]; Roche Diagnostics, Germany) was used as HRP substrate to form a colored reaction product. Absorbance of the resulting reaction product was read at 405 nm with a reference wavelength at 490 nm using a Tecan sunrise plate reader (Männedorf, Switzerland).

All serum samples, positive and negative control samples were analyzed in duplicates and calibrated against reference standard.

Pharmacokinetic (PK) Analysis

The pharmacokinetic parameters were calculated by non-compartmental analysis using WinNonlin™ 1.1.1 (Pharsight, CA, USA).

Briefly, area under the curve ($AUC_{0-inf}$) values were calculated by logarithmic trapezoidal method due to non-linear decrease of the antibodies and extrapolated to infinity using the apparent terminal rate constant λz, with extrapolation from the observed concentration at the last time point.

Plasma clearance was calculated as Dose rate (D) divided by $AUC_{0-inf}$. The apparent terminal half-life (T½) was derived from the equation T½=ln2/λz.

Example 1

Preparation of FcRn Affinity Column

Expression of FcRn in HEK293 Cells

FcRn was transiently expressed by transfection of HEK293 cells with two plasmids containing the coding sequence of FcRn and of beta-2-microglobulin. The transfected cells were cultured in shaker flasks at 36.5° C., 120 rpm (shaker amplitude 5 cm), 80% humidity and 7% $CO_2$. The cells were diluted every 2-3 days to a density of 3 to $4*10^5$ cells/ml.

For transient expression, a 14 l stainless steel bioreactor was started with a culture volume of 8 liters at 36.5° C., pH 7.0±0.2, $pO_2$ 35% (gassing with $N_2$ and air, total gas flow 200 ml $min^{-1}$) and a stirrer speed of 100-400 rpm. When the cell density reached $20*10^5$ cells/ml, 10 mg plasmid DNA (equimolar amounts of both plasmids) was diluted in 400 ml Opti-MEM (Invitrogen). 20 ml of 293fectin (Invitrogen) was added to this mixture, which was then incubated for 15 minutes at room temperature and subsequently transferred into the fermenter. From the next day on, the cells were supplied with nutrients in continuous mode: a feed solution was added at a rate of 500 ml per day and glucose as needed to keep the level above 2 g/l. The supernatant was harvested 7 days after transfection using a swing head centrifuge with 1 l buckets: 4000 rpm for 90 minutes. The supernatant (13 L) was cleared by a Sartobran P filter (0.45 μm+0.2 μm, Sartorius) and the FcRn beta-2-microglobulin complex was purified therefrom.

Biotinylation of Neonatal Fc Receptor 3 mg FcRn beta-2-microglobulin complex were solved/diluted in 5.3 mL 20 mM sodium dihydrogenphosphate buffer containing 150 mM sodium chloride and added to 250 μl PBS and 1 tablet complete protease inhibitor (complete ULTRA Tablets, Roche Diagnostics GmbH). FcRn was biotinylated using the biotinylation kit from Avidity according to the manufacturer instructions (Bulk BIRA, Avidity LLC). The biotinylation reaction was done at room temperature overnight.

The biotinylated FcRn was dialyzed against 20 mM MES buffer comprising 140 mM NaCl, pH 5.5 (buffer A) at 4° C. overnight to remove excess of biotin.

Coupling to Streptavidin Sepharose

For coupling to streptavidin sepharose, 1 mL streptavidin sepharose (GE Healthcare, United Kingdom) was added to the biotinylated and dialyzed FcRn beta-2-microglobulin complex and incubated at 4° C. overnight. The FcRn beta-2-microglobulin complex derivatized sepharose was filled a 4.6 mm×50 mm chromatographic column (Repligen). The column was stored in 80% buffer A and 20% buffer B (20 mM Tris(hydroxymethyl)aminomethane pH 8.8, 140 mM NaCl).

Example 2

Chromatography Using FcRn Affinity Column and pH Gradient

Conditions:

- column dimensions: 50 mm×4.6 mm
- loading: 30 μg sample
- buffer A: 20 mM MES, with 140 mM NaCl, adjusted to pH 5.5 buffer B: 20 mM Tris/HCl, with 140 mM NaCl, adjusted to pH 8.8

30 μg of samples were applied onto the FcRn affinity column equilibrated with buffer A. After a washing step of 10 minutes in 20% buffer B at a flow rate of 0.5 mL/min, elution was performed with a linear gradient from 20% to 70% buffer B over 70 minutes. The UV light absorption at a wavelength of 280 nm was used for detection. The column was regenerated for 10 minutes using 20% buffer B after each run.

For the calculation of relative retention times, a standard sample (anti-Her3 antibody (SEQ ID NO: 03 and 04), oxidized for 18 hours with 0.02% hydrogen peroxide according to (Bertoletti-Ciarlet, A., et al., Mol. Immunol. 46 (2009) 1878-1882) was run at the beginning of a sequence and after each 10 sample injections.

Briefly, the antibody (at 9 mg/mL) in 10 mM sodium phosphate pH 7.0 was mixed with H2O2 to a final concentration of 0.02% and incubated at room temperature for 18 h. To quench the reaction, the samples were thoroughly dialyzed into pre-cooled 10 mM sodium acetate buffer pH 5.0.

Relative retention times were calculated according to the following equation:

$$t_{rel,i} = \frac{t_i - t_{peak2}}{t_{peak3} - t_{peak2}}$$

For peak definition see FIG. 1.

Example 3

Chromatography Using Heparin Affinity Column and pH Gradient

Conditions:

column dimensions: 50 mm×5.0 mm loading: 20-50 μg sample buffer A: 50 mM TRIS pH 7.4 buffer B: 50 mM TRIS pH 7.4, 1000 mM NaCl 20 to 50 μg of protein samples in low-salt buffer (≤25 mM ionic strength) were applied to a TSKgel Heparin-5 PW Glass column, 5.0×50 mm (Tosoh Bioscience, Tokyo/Japan), which was pre-equilibrated with buffer A at room temperature. Elution was performed with a linear gradient from 0-100% buffer B over 32 minutes at a flow rate of 0.8 mg/mL. The UV light absorption at a wavelength of 280 nm was used for detection. Every injection sequence started with a retention time standard (anti-pTau antibody) which was used to calculate relative retention times according to the following formula:

$$t_{rel,i} = \frac{t_i}{t_{pTau}}$$

($t_{rel,i}$: relative retention time of peak i; $t_i$: retention time of peak i; $t_{pTau}$: retention time of the anti-pTau antibody peak).

Example 4

Cynomolgus SDPK Studies

The pharmacokinetics of the test compounds was determined in cynomolgus monkeys following single intravenous administration at dose levels ranging from 0.3 mg/kg to 150 mg/kg. Serial blood samples were collected from the monkeys over several weeks and serum/plasma was prepared from the collected blood samples. Serum/plasma levels of test compounds were determined by ELISA. In case of linear pharmacokinetics pharmacokinetic parameter were determined by standard non-compartmental methods. Clearance was calculated according to following formula:

Clearance=Dose/Area under concentration-time curve

In cases of non-linear pharmacokinetics, the linear fraction of the clearance was determined via following alternative methods: Either clearance values were estimated following IV administration at high dose levels, at which additional non-linear clearance pathways are virtually saturated. Alternatively, PK models comprising a linear and a non-linear, saturable clearance term were established. In these cases, the model-determined linear clearance fraction was used for correlations.

Results:

| antibody no | heparin affinity column rel. retention (vs. pTau) | FcRn affinity column rel. retention (vs. Her3 Pre-peak 1 and Main Peak) | clearance* [mL/kg/day] |
|---|---|---|---|
| 1 | 1 | 0.9 | 61.1 |
| 2 | 1.01 | 3.92 | 5.01 |
| 3 | 0.72 | 0.61 | 3.34 |
| 4 | 0.59 | 0.88 | 3.97 |
| 5 | 0.67 | 0.36 | 3.47 |
| 6 | 0.61 | 0.59 | 5.13 |
| 7 | 0.64 | 0.22 | 6.41 |
| 8 | 0.56 | 2.52 | 4.1 |
| 9 | 0.66 | 0.4 | 5.28 |
| 10 | 0.66 | 1.03 | 4.1 |
| 11 | 0.67 | 0.43 | 5.52 |
| 12 | 0.63 | −0.22 | 1.6 |
| 13 | 0.65 | 1.21 | <8 |
| 14 | 0.44 | 0.29 | 4.73 |
| 15 | 0.26 | −0.46 | 2.4 |
| 16 | 1.05 | 0.52 | >12 |
| 17 | 1 | 1.42 | 24.9 |
| 18 | 0.8 | 3.29 | 90 |
| 19 | 0.99 | 0.78 | 17 |
| 20 | 1.09 | 1.39 | 16.4 |
| 21 | 0.9 | 3.36 | >8 |
| 22 | 0.66 | 0.39 | >8 |
| 23 | 0.53 | 0.61 | 5.37 |
| 24 | 0.13 | −0.199 | 2.5 |
| 25 | 1.01 | 1.78 | 8.16 |
| 26 | 0.26 | −0.16 | 4.81 |
| 27 | 0.53 | 0.37 | 2.45 |
| 28 | 0.59 | 0.17 | 4.8 |
| 29 | 0.52 | 2.43 | 4.87 |
| 30 | 0.79 | 0.58 | 6.3 |
| 31 | 0.55 | 2.24 | 31.92 |
| 32 | 0.77 | 0.42 | 7.5 |
| 33 | 0.52 | 1.91 | 10.08 |
| 34 | 0.55 | 1.86 | 31.92 |
| 35 | 0.84 | 0.01 | 4.63 |

Example 5

Preparation of the Mutants

The following mutants were prepared by site directed mutagenesis of one parent antibody V1 in the Fab: V2, V20, V27, V104 and V108.

5 From these charge variants the following Fc-region variants have been prepared:

| Selection (x = in vivo PK) | | | | | | |
|---|---|---|---|---|---|---|
| | Fv variant | | | | | |
| Fc variant | v104 (even charge distribution) | v20 (negative patch) | v2 (his mutant) | v1 (parent antibody) | v108 (increased patchiness) | v27 (positive patch) |
| AAA(I253A, H310A, H435A) | | | | | | |
| Y436A | | | | | | x |
| WT | x | x | x | x | x | x |
| M428L | | x | | | | |
| T307H/N434H | | x | | | | |
| YTE (M252Y, S254T, T256E) | x | x | x | x | x | x |
| H433K/N434F | | x | | | | |

V2_var 1: M252Y/S254T/T256E = 2-YTE
V20_var 1: M428L = 20-M428L
V20_var 2: T307H/N434H = 20-T307H/N434H
V20_var 3: M252Y/S254T/T256E = 20-YTE
V20_var 4: H433K/N434F = 20-H433K/N434F
V27_var 1: Y436A = 27-Y436A
V27_var 2: M252Y/S254T/T256E = 27-YTE
V104_var 1: M252Y/S254T/T256E = 104-YTE
V108_var 1: M252Y/S254T/T256E = 108-YTE

Example 6

In Vivo Pharmacokinetic Studies

The in vivo studies were conducted using mice lacking the mFcRn α-chain (B6.129X1-Fcgrttm1Dcr/DcrJ; abbreviated FcRn-ko) and homozygous B6.Cg-Fcgrt\tm1Dcr[Tg (FCGRT)32Dcr/DcrJ mice (abbreviated hFcRn Tg32). Mice were given a single intravenous bolus injection of the respective test compound, usually at a dose of 5 mg/kg (n=4-5/compound/mouse strain). Serial blood samples were collected over 4 weeks or 96 h in hFcRn Tg32 and FcRn-ko mice, respectively. Blood samples were allowed to clot and serum was prepared. Serum levels of the respective test compounds were analyzed by ECLIA. Pharmacokinetic evaluation was done using standard non-compartmental pharmacokinetic analysis.

Example 7

Analysis of Serum Samples

The concentrations of the human therapeutic antibodies in murine serum samples were determined using an electro-chemiluminescence immunoassay (ECLIA) method specific for the human Fab moiety of the administered antibody and its variants. Briefly, samples, diluted with assay buffer, were incubated with capture and detection molecules for 9 min at 37° C. Biotinylated mAb<H-Fab (kappa)>M-IgG-Bi was used as capture molecule and a ruthenium(II)tris(bipyridyl) 32+ labeled mAb<H-Fab(CH1)>M-1.19.31-IgG-S-Ru mouse monoclonal antibody was used for detection. Streptavidin-coated magnetic microparticles were added and incubated for additional 9 min at 37° C. to allow complex formation due to biotin-streptavidin interactions. Complexes were magnetically captured on an electrode and a chemiluminescent signal generated using the co-reactant tripropylamine (TPA) was measured by a photomultiplier detector. All serum samples and positive or negative control samples were analyzed in replicates and calibrated against the corresponding antibody that was administered.

The results were as follows:

| variant | FcRn rel. Retention [min] (-wt) | CL (ml/kg/day) Tg32 hFcRn +/+ mice | fold CL change (to WT) in Tg32 hFcRn +/+ |
|---|---|---|---|
| 1-WT | 0 | 5.26 | 1 |
| 1-YTE | 3.72 | 3.69 | 0.70 |
| 104-WT | 0 | 3.67 | 1 |
| 104-YTE | 3.6 | 3.28 | 0.89 |
| 108-WT | 0 | 5.26 | 1 |
| 108-YTE | 3.63 | 4.53 | 0.86 |
| 2-WT | 0 | 3.63 | 1 |
| 2-YTE | 3.64 | 2.72 | 0.75 |
| 20-WT | 0 | 4.02 | 1 |
| 20-H433K/N434F | 7.74 | 6.46 | 1.61 |
| 20-M428L | 1.52 | 2.9 | 0.72 |
| 20-T307H/N434H | 3.75 | 3.21 | 0.8 |
| 20-YTE | 3.48 | 3.03 | 0.75 |
| 27-WT | 0 | 30.1 | 1 |
| 27-Y436A | −0.95 | 30.8 | 1.02 |
| 27-YTE | 4.87 | 18.2 | 0.60 |

Example 8

FcRn Affinity Chromatography Method for Determining Relative Retention Time Differences Between Parent and Modified Antibody Analytical FcRn affinity chromatography was performed using a commercially available FcRn affinity column (Part. No. 08128057001, Roche Diagnostic, Mannheim Germany), pre-equilibrated with 80% buffer A (20 mM MES sodium salt, 140 mM NaCl, pH 5.5) and 20% buffer B (20 mM Tris/HCl, 140 mM NaCl, pH 8.8) at a flow rate of 0.5 mL/min and a column temperature of 25° C. Samples were prepared as above. A total of 30 μg protein was injected. Ten minutes post injection, a linear gradient from 20-100% buffer B over 70 minutes was started. 100% buffer B was held for 10 minutes before the column was re-equilibrated with 80% buffer A and 20% buffer B. Detection was performed with a UV detector set at 280 nm. In order to make results from different runs and different buffer and column lots comparable, and to compensate for slight retention time drifts, a standard sample was measured at the beginning and the end of each sequence and after every 10th run. The relative retention time ($t_{rel}$) was calculated according to equation $$t_{rel,i} = \frac{t_i - t_{peak2}}{t_{peak3} - t_{peak2}}$$

based on the peak definition according to FIG. 1 ($t_{rel,i}$: relative retention time of peak i; $t_i$: retention time of peak i; $t_{peak\ 2}$: retention time of peak 2 of the partially oxidized anti-Her3 antibody according to FIG. 1; $t_{peak\ 3}$: retention time of peak 3 of the anti-Her3 antibody according to FIG. 1).

The invention claimed is:

1. A method for producing an antibody with improved in vivo half-life, comprising the following steps:

a) determining retention time of an antibody in an FcRn affinity chromatography, thereby defining an antibody retention time b) modifying the Fc-region of the antibody by introducing mutations that increase the binding of the Fc-region to human FcRn to obtain a modified antibody, c) determining retention time of the modified antibody in an FcRn affinity chromatography, thereby defining a modified antibody retention time, d) thereby producing the modified antibody with improved in vivo half-life when a relative retention time between the antibody retention time and the modified antibody retention time is more than about 3 minutes and less than about 4 minutes.

2. The method of claim 1, wherein the FcRn affinity chromatography is performed as follows:

using an FcRn affinity chromatography column comprising about 1 mL of a streptavidin agarose matrix with human FcRn conjugated thereto via biotin-streptavidin non-covalent interaction, equilibrated with 80 vol-% buffer A and 20 vol-% buffer B at a flow rate of 0.5 mL/min and a column temperature of 25° C., wherein buffer A comprises 20 mM MES sodium salt, 140 mM NaCl, pH 5.5, wherein buffer B comprises 20 mM Tris/HCl, 140 mM NaCl, pH 8.8;

injecting a total of 30 μg of the reference antibody or the modified antibody prepared in the same mixture of 80 vol-% buffer A and 20 vol-% buffer B on the equilibrated column;

starting at ten minutes post injection, a linear gradient from 20 vol-% to 100 vol-% buffer B over 70 minutes; and determining retention time as measured with a UV detector set at 280 nm.

3. The method of claim 1 further including the step of repeating step b) when the relative retention time is less than about 3 minutes or more than about 4 minutes, whereby in case where the relative retention time is less than 3 minutes, mutations are chosen that result in a further increased binding of the Fc-region to human FcRn, whereby in case the relative retention time is more than 4 minutes, mutations are chosen that result in a less increased binding of the Fc-region to human FcRn.

4. A method for producing an antibody with improved in vivo half-life, comprising the following steps:

a) determining a retention time of a reference antibody in an FcRn affinity chromatography, thereby defining a reference antibody retention time, wherein the reference antibody is an anti-Her3;

b) modifying the Fc-region of the reference antibody by introducing mutations that increase the binding of the Fc-region to human FcRn to obtain a modified antibody;

c) determining a retention time of the modified antibody in an FcRn affinity chromatography, thereby defining a modified antibody retention time; and d) thereby producing the modified antibody with improved in vivo half-life when a relative retention time between the reference antibody retention time and the modified antibody retention time is more than about 3 minutes and less than about 4 minutes.

5. The method of claim 4, wherein the anti-Her3 antibody has a heavy chain with amino acid sequence of SEQ ID NO: 03 and a light chain with amino acid sequence of SEQ ID NO: 04.

6. The method of claim 1, wherein the antibody is an anti-pTau antibody, and the anti-pTau antibody has a heavy chain with amino acid sequence of SEQ ID NO: 01 and a light chain with amino acid sequence of SEQ ID NO: 02.

7. The method of claim 4 further including the step of repeating step b) when the relative retention time is less than about 3 minutes or more than about 4 minutes, whereby in case the relative retention time is less than 3 minutes, mutations are chosen that result in a further increased binding of the Fc-region to human FcRn, whereby in case the relative retention time is more than 4 minutes, mutations are chosen that result in a less increased binding of the Fc-region to human FcRn.

* * * * *

SEQUENCE LISTING

```
<160> NUMBER OF SEQ ID NOS: 33

<210> SEQ ID NO 1
<211> LENGTH: 441
<212> TYPE: PRT
<213> ORGANISM: Artificial Sequence
<220> FEATURE:
<223> OTHER INFORMATION: anti-pTau antibody HC

<400> SEQUENCE: 1

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285
```

-continued

```
Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 2
<211> LENGTH: 218
<212> TYPE: PRT
<213> ORGANISM: Artificial Sequence
<220> FEATURE:
<223> OTHER INFORMATION: anti-pTau antibody LC

<400> SEQUENCE: 2

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215


<210> SEQ ID NO 3
<211> LENGTH: 449
<212> TYPE: PRT
<213> ORGANISM: Artificial Sequence
<220> FEATURE:
<223> OTHER INFORMATION: anti-Her3 antibody HC

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

-continued

```
Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 4
<211> LENGTH: 220
<212> TYPE: PRT
<213> ORGANISM: Artificial Sequence
<220> FEATURE:
<223> OTHER INFORMATION: anti-Her3 antibody LC

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 5
<211> LENGTH: 227
<212> TYPE: PRT
<213> ORGANISM: Homo sapiens
```

<400> SEQUENCE: 5

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Thr Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys
225

<210> SEQ ID NO 6
<211> LENGTH: 326
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

-continued

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 7
<211> LENGTH: 377
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

```
Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 8
<211> LENGTH: 229
<212> TYPE: PRT
<213> ORGANISM: Homo sapiens

<400> SEQUENCE: 8

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

```
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 9
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with the mutations L234A, L235A

<400> SEQUENCE: 9

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 10
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with Y349C, T366S, L368A and Y407V mutations
```

<400> SEQUENCE: 10

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 11
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with S354C, T366W mutations

<400> SEQUENCE: 11

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 12
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and Y349C, T366S, L368A,
      Y407V mutations

<400> SEQUENCE: 12

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
```

-continued

225

<210> SEQ ID NO 13
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a L234A, L235A and S354C, T366W mutations

<400> SEQUENCE: 13

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 14
<211> LENGTH: 227
<212> TYPE: PRT
<213> ORGANISM: Artificial Sequence
<220> FEATURE:
<223> OTHER INFORMATION: human IgG1 Fc-region derived Fc-region polypeptide with a P329G mutation

<400> SEQUENCE: 14

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
```

```
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 15
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A mutations and P329G mutation

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 16
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P239G mutation and Y349C, T366S, L368A, Y407V
      mutations

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with a P329G mutation and S354C, T366W mutation

<400> SEQUENCE: 17
```

-continued

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 18
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G and Y349C, T366S, L368A,
      Y407V mutations

<400> SEQUENCE: 18

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110
```

```
Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 19
<211> LENGTH: 227
<212> TYPE: PRT
<213> ORGANISM: Artificial Sequence
<220> FEATURE:
<223> OTHER INFORMATION: human IgG1 Fc-region derived Fc-region
      polypeptide with L234A, L235A, P329G mutations and S354C, T366W
      mutations

<400> SEQUENCE: 19

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
```

225

<210> SEQ ID NO 20
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P and L235E mutations

<400> SEQUENCE: 20

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 21
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S228P, L235E mutations and P329G mutation

<400> SEQUENCE: 21

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 22
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with S354C, T366W mutations

<400> SEQUENCE: 22

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

-continued

```
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 23
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with Y349C, T366S, L368A, Y407V mutations

<400> SEQUENCE: 23

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 24
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and S354C, T366W mutations

<400> SEQUENCE: 24
```

-continued

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 25
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a S228P, L235E and Y349C, T366S, L368A, Y407V
      mutations

<400> SEQUENCE: 25

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
```

```
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 26
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G mutation

<400> SEQUENCE: 26

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 27
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P239G and Y349C, T366S, L368A, Y407V mutations

<400> SEQUENCE: 27

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Cys Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 28
<211> LENGTH: 229
<212> TYPE: PRT
<213> ORGANISM: Artificial Sequence
<220> FEATURE:
<223> OTHER INFORMATION: human IgG4 Fc-region derived Fc-region
      polypeptide with a P329G and S354C, T366W mutations

<400> SEQUENCE: 28

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

-continued

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Gly Ser
100 105 110

Ser Ile Glu Lys Thr Ile Ser Lys Ala Lys Gly Gln Pro Arg Glu Pro
115 120 125

Gln Val Tyr Thr Leu Pro Pro Cys Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 29
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and Y349C, T366S, L368A, Y407V mutations

<400> SEQUENCE: 29

Glu Ser Lys Tyr Gly Pro Pro Cys Pro Pro Cys Pro Ala Pro Glu Phe
1 5 10 15

Glu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Gly Ser
100 105 110

Ser Ile Glu Lys Thr Ile Ser Lys Ala Lys Gly Gln Pro Arg Glu Pro
115 120 125

Gln Val Cys Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu

```
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 30
<211> LENGTH: 229
<212> TYPE: PRT
<213> ORGANISM: Artificial Sequence
<220> FEATURE:
<223> OTHER INFORMATION: human IgG4 Fc-region derived Fc-region polypeptide with a S228P, L235E, P329G and S354C, T366W mutations

<400> SEQUENCE: 30

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Cys Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 31
<211> LENGTH: 274
<212> TYPE: PRT
<213> ORGANISM: Homo sapiens

<400> SEQUENCE: 31

```
Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
```

```
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
            260                 265                 270

Ser Ser


<210> SEQ ID NO 32
<211> LENGTH: 21
<212> TYPE: PRT
<213> ORGANISM: Artificial Sequence
<220> FEATURE:
<223> OTHER INFORMATION: HIS-AVITAG

<400> SEQUENCE: 32

His His His His His His Gly Leu Asn Asp Ile Phe Glu Ala Gln Lys
1               5                   10                  15

Ile Glu Trp His Glu
            20


<210> SEQ ID NO 33
<211> LENGTH: 99
<212> TYPE: PRT
<213> ORGANISM: Homo sapiens

<400> SEQUENCE: 33

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30
```

-continued

```
Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```